US007429644B2

(12) United States Patent
Garber et al.

(10) Patent No.: US 7,429,644 B2
(45) Date of Patent: Sep. 30, 2008

(54) HUMANIZED ANTI-LT-β-R ANTIBODIES

(75) Inventors: Ellen Garber, Cambridge, MA (US); Paul Lyne, Allston, MA (US); Jose William Saldanha, Enfield (GB)

(73) Assignee: Biogen Idec MA Inc., Cambridge, MA (US)

( * ) Notice: Subject to any disclaimer, the term of this patent is extended or adjusted under 35 U.S.C. 154(b) by 520 days.

(21) Appl. No.: 10/412,406

(22) Filed: Apr. 10, 2003

(65) Prior Publication Data

US 2004/0058394 A1     Mar. 25, 2004

Related U.S. Application Data

(63) Continuation of application No. PCT/US01/32140, filed on Oct. 12, 2001.

(60) Provisional application No. 60/299,987, filed on Jun. 21, 2001, provisional application No. 60/275,289, filed on Mar. 13, 2001, provisional application No. 60/240,285, filed on Oct. 13, 2000.

(51) Int. Cl.
*C12P 21/08* (2006.01)
*C07K 16/00* (2006.01)
*A61K 39/395* (2006.01)
*C12P 21/04* (2006.01)
*C07H 21/04* (2006.01)

(52) U.S. Cl. ............ 530/387.3; 530/388.1; 530/388.22; 424/133.1; 424/141.1; 424/143.1; 435/69.6; 435/70.21

(58) Field of Classification Search .............. 530/387.3, 530/388.1, 388.22, 388.8; 424/133.1, 141.1, 424/143.1, 155.1; 435/69.1, 69.6, 70.21
See application file for complete search history.

(56) References Cited

U.S. PATENT DOCUMENTS

| 5,530,101 | A | * | 6/1996 | Queen et al. |
| 5,618,920 | A | * | 4/1997 | Robinson et al. |
| 5,859,205 | A | | 1/1999 | Adair et al. |
| 5,925,351 | A | | 7/1999 | Browning et al. |
| 6,312,691 | B1 | | 11/2001 | Browning et al. |
| 6,403,087 | B1 | | 6/2002 | Browning et al. |
| 6,669,941 | B1 | | 12/2003 | Browning et al. |
| 7,001,598 | B2 | | 2/2006 | Browning et al. |
| 7,060,667 | B1 | | 6/2006 | Browning et al. |
| 2005/0037003 | A1 | | 2/2005 | Browning et al. |
| 2005/0281811 | A1 | | 12/2005 | Browning et al. |
| 2006/0104971 | A1 | | 5/2006 | Garber et al. |
| 2006/0134102 | A1 | | 6/2006 | LePage et al. |
| 2006/0222644 | A1 | | 10/2006 | Garber et al. |
| 2006/0280722 | A1 | | 12/2006 | Browning et al. |

FOREIGN PATENT DOCUMENTS

| EP | 0519596 B1 | 12/1992 |
| EP | 0519596 B1 | 2/2005 |
| WO | WO 92/00329 A1 | 1/1992 |
| WO | WO 94/04679 A1 | 3/1994 |
| WO | WO 94/13808 A2 | 6/1994 |
| WO | WO 94/13808 A3 | 6/1994 |
| WO | WO 96/22788 A1 | 8/1996 |
| WO | WO-91/09967 A1 | 7/1997 |
| WO | WO 99/38525 A1 | 8/1999 |
| WO | WO-99/58679 A1 | 11/1999 |

OTHER PUBLICATIONS

Kreitman et al. Advanced Drug Delivery Reviews, 31:53-88, 1998.*
William E. Paul. Fundamental Immunology, 3rd ed., p. 242, 1993.*
Paul, W. E., Fundamental Immunology, pp. 292-295, 1993.*
Rudikoff et al. Proc. Natl. Acad. Sci. USA, 79(6):1979-1983, 1982.*
Browning et al. "Characterization of surface lymphotoxin forms. Use of specific monoclonal antibodies and soluble receptors." *J Immunol.* Jan. 1, 1995;154(1):33-46.
Browning et al. "Signaling through the lymphotoxin β receptor induces the death of some adenocarcinoma tumor lines." *J Exp Med.* Mar. 1, 1996;183(3):867-78.
Couto et al. "Humanization of KC4G3, an anti-human carcinoma antibody." *Hybridoma.* Jun. 1994;13(3):215-9.
Foote et al. "Antibody framework residues affecting the conformation of the hypervariable loops." *J Mol Biol.* Mar. 20, 1992;224(2):487-99.
Kolbinger et al. "Humanization of a mouse anti-human IgE antibody: a potential therapeutic for IgE-mediated allergies." *Protein Eng.* Nov. 1993;6(8):971-80.
He, Xiaozhong et al. "General Introduction to Modern Biological Technique" *Publishing House of Beijing Normal University*, 1st Edition, pp. 254-256 (1.8.3 & 1.8.4).
Riechmann, Lutz et al., "Reshaping human antibodies for therapy," *Nature*, vol. 332:323-327 (1998).
Tempest, Philip R. et al., "Reshaping a Human Monoclonal Antibody To Inhibit Human Respiratory Syncytial Virus Infection In Vivo," *Biotechnology*, vol. 9:266-271 (1991).
Alderson, Mark R. et al., "Regulation of apoptosis and T cell activation by Fas-specific mAb," *International Immunology*, vol. 6(11):1799-1806 (1994).
Androlewicz, Matthew J. et al., "Lymphotoxin Is Expressed as a Heteromeric Complex with a Distinct 33-kDa Glycoprotein on the Surface of an Activated Human T Cell Hybridoma," *The Journal of Biological Chemistry*, vol. 267(4):2542-2547 (1992).
Arulanandam, Antonio R.N. et al., "A Soluble Multimeric Recombinant CD2 Protein Identifies CD48 as a Low Affinity Ligand for Human CD2: Divergence of CD2 Ligands during the Evolution of Humans and Mice," *J. Exp. Med.*, vol. 177:1439-1450 (1993).
Bernstein, David L. et al., "Effects of therapy with an immunomodulator (imiquimod, R-837) alone and with acyclovir on genital HSV-2 infection in guinea-pigs when begun after lesion development," *Antiviral Research*, vol. 20:45-55 (1993).
Browning, Jeffrey L. et al., "Lymphotoxin and an Associated 33-kDa Glycoprotein are Expressed on the Surface of an Activated Human T Cell Hybridoma," *The Journal of Immunology*, vol. 147(4):1230-1237 (1991).

(Continued)

*Primary Examiner*—David J. Blanchard
(74) *Attorney, Agent, or Firm*—Lahive and Cockfield, LLP; Amy E. Mandragouras, Esq.; Cristin Howley Cowles

(57) ABSTRACT

Humanized antibodies to LT-β-R and methods of use thereof are provided.

33 Claims, 9 Drawing Sheets

OTHER PUBLICATIONS

Browning, Jeffrey L. et al., "Lymphotoxin β, a Novel Member of the TNF Family That Forms a Heteromeric Complex with Lymphotoxin on the Cell Surface," *Cell*, vol. 72:847-856 (1993).

Browning, Jeffrey L. et al., "Signaling through the Lymphotoxin-β Receptor in Conjunction with Interferon-γ Induces the Death of a Human Tumor Line," *The 9th International Congress of Immunology*, pp. 772, No. 4582 (1995).

Browning, Jeffrey L. et al., "Studies on the Differing Effects of Tumor Necrosis Factor and Lymphotoxin on the Growth of Several Human Tumor Lines," *The Journal of Immunology*, vol. 143(6):1859-1867 (1989).

Crowe, Paul D. et al., "A Lymphotoxin-β-Specific Receptor," *Science*, vol. 264:707-710 (1994).

Crowe, Paul D. et al., "Production of lymphotoxin (LTα) and a soluble dimeric form of its receptor using the baculovirus expression system," *Journal of Immunological Methods*, vol. 168:79-89 (1994).

Dhein, Jens et al., "Induction of Apoptosis by Monoclonal Antibody Anti-Apo-1 Class Switch Variants is Dependent on Cross-Linking of Apo-1 Cell Surface Antigens," *The Journal of Immunology*, vol. 149(10):3166-3173 (1992).

Dighe, Anand S. et al., "Enhanced In Vivo Growth and Resistance to Rejection of Tumor Cells Expressing Dominant Negative IFNγ Receptors," *Immunity*, vol. 1:447-456 (1994).

Düzgünes, Nejat et al., "Liposome Targeting to HIV-Infected Cells Via Recombinant Soluble CD4 and CD4-IgG (Immunoadhesin)," *Journal of Cellular Biochemistry*, vol. 16E:77 (1992).

Eppstein, Deborah A. et al., "Biological activity of liposome-encapsulated murine interferon γ is mediated by a cell membrane receptor," *Proc. Natl. Acad. Sci. USA*, vol. 82:3688-3692 (1985).

Fukushima, Keiko et al., "N-Linked Sugar Chain Structure of Recombinant Human Lymphotoxin Produced by CHO Cells: The Functional Role of Carbohydrate as to Its Lectin-like Character and Clearance Velocity," *Archives of Biochemistry and Biophysics*, vol. 304(1):144-153 (1993).

Havell, Edward A. et al., "The Antitumor Function of Tumor Necrosis Factor (TNF), I. Therapeutic Action of TNF against an Established Murine Sarcoma Is Indirect, Immunologically Dependent, and Limited by Severe Toxicity," *J. Exp. Med.*, vol. 167:1067-1085 (1988).

Hwang, Karl J. et al., "Hepatic uptake and degradation of unilamellar sphingomyelin/cholesterol liposomes: A kinetic study," *Proc. Natl. Acad. Sci. USA*, vol. 77(7):4030-4034 (1980).

Johne, Berit et al., "Epitope mapping and binding kinetics of monoclonal antibodies studied by real time biospecific interaction analysis using surface plasmon resonance," *Journal of Immunological Methods*, vol. 160:191-198 (1993).

Jurásková, Vera et al., "Interferon inducer, polyriboguanylic-polyribocytidylic acid, inhibits experimental hepatic metastases in mice," *European Journal of Pharmacology*, vol. 221:107-111 (1992).

Kawabe, Tsutomu et al., "The Immune Responses in CD40-Deficient Mice: Impaired Immunoglobulin Class Switching and Germinal Center Formation," *Immunity*, vol. 1:167-178 (1994).

Kolanus, Waldemar et al., "T Cell Activation by Clustered Tyrosine Kinases," *Cell*, vol. 74:171-183 (1993).

Kopp, William C. et al., "Immunomodulatory Effects of Interferon-γ in Patients with Metastatic Malignant Melanoma," *J. of Immunother.*, vol. 13:181-190 (1993).

Lane, Peter et al., "Activated human T cells express a ligand for the human B cell-associated antigen CD40 which participates in T cell-dependent activation of B lymphocytes," *Eur. J. Immunol.*, vol. 22:2573-2578 (1992).

Langer, Robert et al., "Biocompatibility of polymeric delivery systems for macromolecules," *Journal of Biomedical Meterials Research*, vol. 15:267-277 (1981).

Langer, Robert et al., "Controlled release of macromolecules," *Chemtech.*, vol. 12:98-105 (1982).

Ling, Leona E. et al., "Human Type I Interferon Receptor, IFNAR, Is a Heavily Glycosylated 120-130 kD Membrane Protein," *Journal of Interferon and Cytokine Research*, vol. 15:55-61 (1995).

Loetscher, Hansruedi et al., "Recombinant 55-kDa Tumor Necrosis Factor (TNF) Receptor," *The Journal of Biological Chemistry*, vol. 266(27):18324-18329 (1991).

Morrison, Sherie L. et al., "Chimeric human antibody molecules: Mouse antigen-binding domains with human constant region domains," *Proc. Natl. Acad. Sci. USA*, vol. 81:6851-6855 (1984).

Niederle, Norbert et al., "Long-Term Treatment of Chronic Myelogenous Leukemia with Different Interferons: Results from Three Studies," *Leukemia and Lymphoma*, vol. 9:111-119 (1993).

Onishi, Tetsuro et al., "A Study on Direct Antitumor Activity of Bropirimine (Oral Interferon Inducer) for Renal Cell Carcinoma," *Acta Urol. Jpn.*, vol. 40:195-200 (1994).

Pleskov, V.M. et al., "The receptor-mediated endocytosis of influenza viruses and low-density lipoproteins by tissue cells," *Vopr. Virusol.*, vol. 39(3):121-125 (1994).

Queen, Cary et al., "A humanized antibody that binds to the interleukin 2 receptor," *Proc. Natl. Acad. Sci. USA*, vol. 86:10029-10033 (1989).

Raitano, Arthur B. et al., "Tumor Necrosis Factor Up-regulates γ-Interferon Binding in a Human Carcinoma Cell Line," *The Journal of Biological Chemistry*, vol. 265(18):10466-10472 (1990).

Schiller, Joan H. et al., "Biological and Clinical Effects of Intravenous Tumor Necrosis Factor-α Administered Three Times Weekly," *Cancer Research*, vol. 51:1651-1658 (1991).

Schoenfeld, Hans-Joachim et al., "Efficient Purification of Recombinant Human Tumor Necrosis Factor β from *Escherichia coli* Yields Biologically Active Protein with a Trimeric Structure That Binds to Both Tumor Necrosis Factor Receptors," *The Journal of Biological Chemistry*, vol. 266(6):3863-3869 (1991).

Sidman, Kenneth R. et al., "Controlled Release of Macromolecules and Pharmaceuticals from Synthetic Polypeptides Based on Glutamic Acid," *Biopolymers*, vol. 22:547-556 (1983).

Slepushkin, A.N. et al., "A comparative study of live and inactivated influenza vaccines: the organization of the observation and the results of a study of their reactogenicity and immunogenicity," *Vopr. Virusol.*, vol. 39(3):129-131 (1994).

Traunecker, André et al., "Highly efficient neutralization of HIV with recombinant CD4-immunoglobulin molecules," *Nature*, vol. 339:68-70 (1989).

Ullrich, Axel et al., "Signal Transduction by Receptors with Tyrosine Kinase Activity," *Cell*, vol. 61:203-212 (1990).

Winter, Greg et al., "Man-made antibiotics," *Nature*, vol. 349:293-299 (1991).

Xu, J. et al., "Mice deficient for the CD40 ligand," *Immunity*, vol. 1(5):423-431 (1994).

Yonehara, Shin et al., "A Cell-killing Monoclonal Antibody (Anti-Fas) to a Cell Surface Antigen Co-downregulated with the Receptor of Tumor Necrosis Factor," *J. Exp. Med.*, vol. 169:1747-1756 (1989).

Jain et al., *Cancer and Metastasis Reviews* 9:253-266(1990).

Hipp et al., "Cancer Vaccines: An Update" in vivo 14:571-585 (2000).

Campbell, Neil A. et al., "Methods: Monoclonal Antibody Technology," *Biology*, 5th Edition, Unit Seven, Animal Form and Function, Benjamin/Cummings, Laura Kenney Ed., p. 856 (1999).

Co, Man Sung et al., "Humanized antibodies for therapy," *Nature*, vol. 351:501-502 (1991).

Colman, P.M., "Effects of amino acid sequence changes on antibody-antigen interactions," *Research in Immunology*, vol. 145:33-36 (1994).

Riechmann, Lutz et al., "Reshaping human antibodies for therapy," *Nature*, vol. 332:323-327 (1988).

Tempest, Philip R. et al., "Reshaping a Human Monoclonal Antibody to Inhibit Human Respiratory Syncytial Virus Infection In Vivo," *Bio/Technology*, vol. 9:266-271 (1991).

* cited by examiner

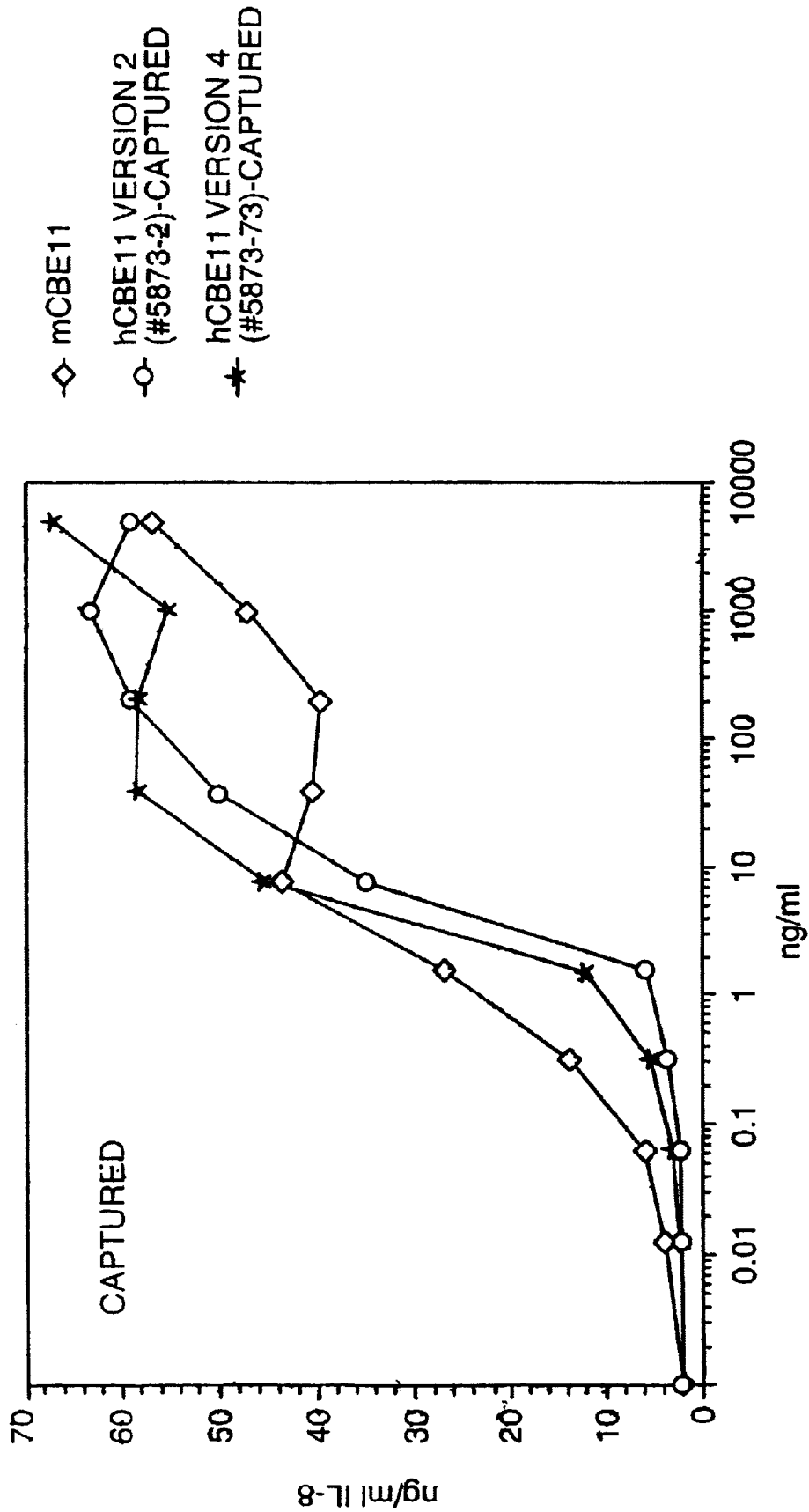

SEQUENCE LISTING

```
<160> NUMBER OF SEQ ID NOS: 33

<210> SEQ ID NO 1
<211> LENGTH: 107
<212> TYPE: PRT
<213> ORGANISM: murine

<400> SEQUENCE: 1

Asp Ile Lys Met Thr Gln Ser Pro Ser Met Tyr Ala Ser Leu Gly
1               5                   10                  15

Glu Arg Val Thr Ile Thr Cys Lys Ala Gly Gln Asp Ile Lys Ser Tyr
                20                  25                  30

Leu Ser Trp Tyr Gln Gln Lys Pro Trp Lys Ser Pro Lys Ile Leu Ile
            35                  40                  45
```

```
Tyr Tyr Ala Thr Arg Leu Ala Asp Gly Val Pro Ser Arg Phe Ser Gly
         50                  55                  60

Ser Gly Ser Gly Gln Asp Tyr Ser Leu Thr Ile Ser Ser Leu Glu Ser
 65                  70                  75                  80

Asp Asp Thr Ala Thr Tyr Tyr Cys Leu Gln His Gly Glu Ser Pro Trp
                 85                  90                  95

Thr Phe Gly Gly Gly Thr Lys Leu Glu Ile Lys
            100                 105
```

<210> SEQ ID NO 2
<211> LENGTH: 120
<212> TYPE: PRT
<213> ORGANISM: murine

<400> SEQUENCE: 2

```
Glu Val Gln Leu Val Glu Ser Gly Gly Gly Leu Val Lys Pro Gly Gly
 1               5                  10                  15

Ser Leu Lys Leu Ser Cys Ala Ala Ser Gly Phe Thr Phe Ser Asp Tyr
             20                  25                  30

Tyr Met Tyr Trp Phe Arg Gln Thr Pro Glu Lys Arg Leu Glu Trp Val
         35                  40                  45

Ala Thr Ile Ser Asp Gly Gly Ser Tyr Thr Tyr Tyr Pro Asp Ser Val
     50                  55                  60

Lys Gly Arg Phe Thr Ile Ser Arg Asp Asn Ala Lys Asn Asn Leu Tyr
 65                  70                  75                  80

Leu Gln Met Ser Ser Leu Lys Ser Glu Asp Thr Ala Met Tyr Tyr Cys
                 85                  90                  95

Val Arg Glu Glu Asn Gly Asn Phe Tyr Tyr Phe Asp Tyr Trp Gly Gln
            100                 105                 110

Gly Thr Thr Val Thr Val Ser Ser
        115                 120
```

<210> SEQ ID NO 3
<211> LENGTH: 321
<212> TYPE: DNA
<213> ORGANISM: Homo Sapien

<400> SEQUENCE: 3

```
gatattaaga tgacccagtc tccatcatcc ttgtctgcat cggtgggaga cagggtcact    60
atcacttgca aggcgggtca ggacattaaa agctatttaa gctggtacca gcagaaacca   120
tggaaagcgc ctaagatcct gatctattat gcaacaaggt tggcagatgg ggtcccatca   180
agattcagtg gcagtggatc tgggcaagat tatactctaa ccatcagcag cctgcagcct   240
gaggatttcg caacttatta ctgtctacag catggtgaga gcccgtggac gttcggtgga   300
ggcaccaagc tggagatcaa a                                             321
```

<210> SEQ ID NO 4
<211> LENGTH: 107
<212> TYPE: PRT
<213> ORGANISM: Homo Sapien

<400> SEQUENCE: 4

```
Asp Ile Lys Met Thr Gln Ser Pro Ser Ser Leu Ser Ala Ser Val Gly
 1               5                  10                  15

Asp Arg Val Thr Ile Thr Cys Lys Ala Gly Gln Asp Ile Lys Ser Tyr
             20                  25                  30
```

```
Leu Ser Trp Tyr Gln Gln Lys Pro Trp Lys Ala Pro Lys Ile Leu Ile
        35                  40                  45

Tyr Tyr Ala Thr Arg Leu Ala Asp Gly Val Pro Ser Arg Phe Ser Gly
 50                  55                  60

Ser Gly Ser Gly Gln Asp Tyr Thr Leu Thr Ile Ser Ser Leu Gln Pro
 65                  70                  75                  80

Glu Asp Phe Ala Thr Tyr Tyr Cys Leu Gln His Gly Glu Ser Pro Trp
                 85                  90                  95

Thr Phe Gly Gly Gly Thr Lys Leu Glu Ile Lys
            100                 105
```

<210> SEQ ID NO 5
<211> LENGTH: 321
<212> TYPE: DNA
<213> ORGANISM: Homo Sapien

<400> SEQUENCE: 5

```
gatatccaga tgacccagtc tccatcatcc ttgtctgcat cggtgggaga cagggtcact      60
atcacttgca aggcgggtca ggacattaaa agctatttaa gctggtacca gcagaaacca     120
tggaaagcgc ctaagatcct gatctattat gcaacaaggt tggcagatgg ggtcccatca     180
agattcagtg gcagtggatc tggtacagat tatactctaa ccatcagcag cctgcagcct     240
gaggatttcg caacttatta ctgtctacag catggtgaga gcccgtggac gttcggtgga     300
ggcaccaagc tggagatcaa a                                               321
```

<210> SEQ ID NO 6
<211> LENGTH: 107
<212> TYPE: PRT
<213> ORGANISM: Homo Sapien

<400> SEQUENCE: 6

```
Asp Ile Gln Met Thr Gln Ser Pro Ser Ser Leu Ser Ala Ser Val Gly
 1               5                  10                  15

Asp Arg Val Thr Ile Thr Cys Lys Ala Gly Gln Asp Ile Lys Ser Tyr
            20                  25                  30

Leu Ser Trp Tyr Gln Gln Lys Pro Trp Lys Ala Pro Lys Ile Leu Ile
        35                  40                  45

Tyr Tyr Ala Thr Arg Leu Ala Asp Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Leu Gln His Gly Glu Ser Pro Trp
                 85                  90                  95

Thr Phe Gly Gly Gly Thr Lys Leu Glu Ile Lys
            100                 105
```

<210> SEQ ID NO 7
<211> LENGTH: 321
<212> TYPE: DNA
<213> ORGANISM: Homo Sapien

<400> SEQUENCE: 7

```
gatatccaga tgacccagtc tccatcatcc ttgtctgcat cggtgggaga cagggtcact      60
atcacttgca aggcgggtca ggacattaaa agctatttaa gctggtacca gcagaaacca     120
gggaaagcgc ctaagcctct gatctattat gcaacaaggt tggcagatgg ggtcccatca     180
agattcagtg gcagtggatc tggtacagat tatactctaa ccatcagcag cctgcagcct     240
```

-continued gaggatttcg caacttatta ctgtctacag catggtgaga gcccgtggac gttcggtgga     300
ggcaccaagc tggagatcaa a     321

<210> SEQ ID NO 8
<211> LENGTH: 107
<212> TYPE: PRT
<213> ORGANISM: Homo Sapien

<400> SEQUENCE: 8

Asp Ile Gln Met Thr Gln Ser Pro Ser Ser Leu Ser Ala Ser Val Gly
1                   5                    10                 15

Asp Arg Val Thr Ile Thr Cys Lys Ala Gly Gln Asp Ile Lys Ser Tyr
              20                    25                    30

Leu Ser Trp Tyr Gln Gln Lys Pro Gly Lys Ala Pro Lys Leu Leu Ile
            35                    40                  45

Tyr Tyr Ala Thr Arg Leu Ala Asp Gly Val Pro Ser Arg Phe Ser Gly
    50                    55                    60

Ser Gly Ser Gly Thr Asp Tyr Thr Leu Thr Ile Ser Ser Leu Gln Pro
65                   70                    75                    80

Glu Asp Phe Ala Thr Tyr Tyr Cys Leu Gln His Gly Glu Ser Pro Trp
              85                    90                    95

Thr Phe Gly Gly Gly Thr Lys Leu Glu Ile Lys
            100                    105

<210> SEQ ID NO 9
<211> LENGTH: 360
<212> TYPE: DNA
<213> ORGANISM: Homo Sapien

<400> SEQUENCE: 9
gaggtacaac tggtggagtc tgggggaggc ttagtgaagc ctggagggtc cctgaggctc     60
tcctgtgcag cctctggatt cactttcagt gactattaca tgtattggtt tcgccagact     120
ccgggaaagg ggctggagtg ggtcgcaacc attagtgatg gtggtagtta cacctactat     180
ccagacagtg tgaaggggcg attcaccatc tccagagaca atgccaagaa cagcctctac     240
ctgcagatga gcagcctgag gctgaggac acagccatgt attactgtgt aagagaggag     300
aatggtaact tttactactt tgactactgg ggccaaggga ccacggtcac cgtctcctca     360

<210> SEQ ID NO 10
<211> LENGTH: 120
<212> TYPE: PRT
<213> ORGANISM: Homo Sapien

<400> SEQUENCE: 10

Glu Val Gln Leu Val Glu Ser Gly Gly Gly Leu Val Lys Pro Gly Gly
1                   5                    10                 15

Ser Leu Arg Leu Ser Cys Ala Ala Ser Gly Phe Thr Phe Ser Asp Tyr
              20                    25                    30

Tyr Met Tyr Trp Phe Arg Gln Thr Pro Gly Lys Gly Leu Glu Trp Val
            35                    40                  45

Ala Thr Ile Ser Asp Gly Gly Ser Tyr Thr Tyr Tyr Pro Asp Ser Val
    50                    55                    60

Lys Gly Arg Phe Thr Ile Ser Arg Asp Asn Ala Lys Asn Ser Leu Tyr
65                   70                    75                    80

Leu Gln Met Ser Ser Leu Arg Ala Glu Asp Thr Ala Met Tyr Tyr Cys
              85                    90                    95

Val Arg Glu Glu Asn Gly Asn Phe Tyr Tyr Phe Asp Tyr Trp Gly Gln
            100                 105                 110

Gly Thr Thr Val Thr Val Ser Ser
        115                 120

<210> SEQ ID NO 11
<211> LENGTH: 360
<212> TYPE: DNA
<213> ORGANISM: Homo Sapien

<400> SEQUENCE: 11
gaggtacaac tggtggagtc tgggggaggc ttagtgaagc ctggagggtc cctgaggctc      60
tcctgtgcag cctctggatt cactttcagt gactattaca tgtattggtt tcgccaggcc     120
ccgggaaagg ggctggagtg ggtcgcaacc attagtgatg gtggtagtta cacctactat     180
ccagacagtg tgaaggggcg attcaccatc tccagagaca atgccaagaa cagcctctac     240
ctgcagatga gcagcctgag ggctgaggac acagctgtgt attactgtgt aagagaggag     300
aatggtaact tttactactt tgactactgg ggccaaggga ccacggtcac cgtctcctca     360

<210> SEQ ID NO 12
<211> LENGTH: 120
<212> TYPE: PRT
<213> ORGANISM: Homo Sapien

<400> SEQUENCE: 12

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asp Tyr
             20                  25                  30

Tyr Met Tyr Trp Phe Arg Gln Ala Pro Gly Lys Gly Leu Glu Trp Val
         35                  40                  45

Ala Thr Ile Ser Asp Gly Gly Ser Tyr Thr Tyr Tyr Pro Asp Ser Val
     50                  55                  60

Lys Gly Arg Phe Thr Ile Ser Arg Asp Asn Ala Lys Asn Ser Leu Tyr
 65                  70                  75                  80

Leu Gln Met Ser Ser Leu Arg Ala Glu Asp Thr Ala Val Tyr Tyr Cys
             85                  90                  95

Val Arg Glu Glu Asn Gly Asn Phe Tyr Tyr Phe Asp Tyr Trp Gly Gln
            100                 105                 110

Gly Thr Thr Val Thr Val Ser Ser
        115                 120

<210> SEQ ID NO 13
<211> LENGTH: 360
<212> TYPE: DNA
<213> ORGANISM: Homo Sapien

<400> SEQUENCE: 13
gaggtacaac tggtggagtc tgggggaggc ttagtgaagc ctggagggtc cctgaggctc      60
tcctgtgcag cctctggatt cactttcagt gactattaca tgtattggtt tcgccaggcc     120
ccgggaaagg ggctggagtg ggtcgcaacc attagtgatg gtggtagtta cacctactat     180
ccagacagtg tgaaggggcg attcaccatc tccagagaca atgccaagaa cagcctctac     240
ctgcagatga gcagcctgag ggctgaggac acagctgtgt attactgtgt aagagaggag     300
aatggtaact tttactactt tgactactgg ggccaaggga ccacggtcac cgtctcctca     360

<210> SEQ ID NO 14
<211> LENGTH: 120
<212> TYPE: PRT
<213> ORGANISM: Homo Sapien

<400> SEQUENCE: 14

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Thr Ile Ser Asp Gly Gly Ser Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Val Tyr Tyr Cys
                85                  90                  95

Ala Arg Glu Glu Asn Gly Asn Phe Tyr Tyr Phe Asp Tyr Trp Gly Gln
            100                 105                 110

Gly Thr Thr Val Thr Val Ser Ser
        115                 120

<210> SEQ ID NO 15
<211> LENGTH: 360
<212> TYPE: DNA
<213> ORGANISM: Homo Sapien

<400> SEQUENCE: 15
gaggtacaac tggtggagtc tgggggaggc ttagtgaagc ctggagggtc cctgaggctc      60
tcctgtgcag cctctggatt cactttcagt gactattaca tgtattggtt tcgccaggcc     120
ccgggaaagg ggctggagtg ggtcgcaacc attagtgatg gtggtagtta cacctactat     180
ccagacagtg tgaaggggcg attcaccatc tccagagaca atgccaagaa cagcctctac     240
ctgcagatga gcagcctgag ggctgaggac acagctgtgt attactgcgc aagagaggag     300
aatggtaact tttactactt tgactactgg ggccaaggga ccacggtcac cgtctcctca     360

<210> SEQ ID NO 16
<211> LENGTH: 120
<212> TYPE: PRT
<213> ORGANISM: Homo Sapien

<400> SEQUENCE: 16

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Tyr Trp Phe Arg Gln Ala Pro Gly Lys Gly Leu Glu Trp Val
        35                  40                  45

Ala Thr Ile Ser Asp Gly Gly Ser Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Val Tyr Tyr Cys
                85                  90                  95

```
Ala Arg Glu Glu Asn Gly Asn Phe Tyr Tyr Phe Asp Tyr Trp Gly Gln
            100                 105                 110

Gly Thr Thr Val Thr Val Ser Ser
        115                 120
```

<210> SEQ ID NO 17
<211> LENGTH: 36
<212> TYPE: DNA
<213> ORGANISM: Homo Sapien

<400> SEQUENCE: 17
gcctggaggg tccctgaggc tctcctgtgc agcctc                                36

<210> SEQ ID NO 18
<211> LENGTH: 42
<212> TYPE: DNA
<213> ORGANISM: Homo Sapien

<400> SEQUENCE: 18
gtttcgccag actccgggaa aggggctgga gtgggtcgca ac                         42

<210> SEQ ID NO 19
<211> LENGTH: 67
<212> TYPE: DNA
<213> ORGANISM: Homo Sapien

<400> SEQUENCE: 19
cagagacaat gccaagaaca gcctctacct gcagatgagc agcctgaggg ctgaggacac      60
agccatg                                                                67

<210> SEQ ID NO 20
<211> LENGTH: 38
<212> TYPE: DNA
<213> ORGANISM: Homo Sapien

<400> SEQUENCE: 20
catgtattgg tttcgccagg ccccgggaaa ggggctgg                              38

<210> SEQ ID NO 21
<211> LENGTH: 36
<212> TYPE: DNA
<213> ORGANISM: Homo Sapien

<400> SEQUENCE: 21
gggctgagga cacagctgtg tattactgtg taagag                                36

<210> SEQ ID NO 22
<211> LENGTH: 50
<212> TYPE: DNA
<213> ORGANISM: Homo Sapien

<400> SEQUENCE: 22
gtgactatta catgtattgg gtgcgccagg ccccgggaaa ggggctggag                 50

<210> SEQ ID NO 23
<211> LENGTH: 52
<212> TYPE: DNA
<213> ORGANISM: Homo Sapien

<400> SEQUENCE: 23
gagggctgag gacacagctg tgtattactg cgcaagagag gagaatggta ac              52

<210> SEQ ID NO 24
<211> LENGTH: 64
<212> TYPE: DNA
<213> ORGANISM: Homo Sapien

<400> SEQUENCE: 24
cttgcaagtg atagtgaccc tgtctcccac cgatgcagac aaggatgatg gagactgggt    60
catc    64

<210> SEQ ID NO 25
<211> LENGTH: 43
<212> TYPE: DNA
<213> ORGANISM: Homo Sapien

<400> SEQUENCE: 25
cataatagat caggatctta ggcgctttcc atggtttctg ctg    43

<210> SEQ ID NO 26
<211> LENGTH: 72
<212> TYPE: DNA
<213> ORGANISM: Homo Sapien

<400> SEQUENCE: 26
gtagacagta ataagttgcg aaatcctcag gctgcaggct gctgatggtt agagtataat    60
cttgcccaga tc    72

<210> SEQ ID NO 27
<211> LENGTH: 40
<212> TYPE: DNA
<213> ORGANISM: Homo Sapien

<400> SEQUENCE: 27
gatggagact gggtcatctg gatatcacct ctggcacctg    40

<210> SEQ ID NO 28
<211> LENGTH: 40
<212> TYPE: DNA
<213> ORGANISM: Homo Sapien

<400> SEQUENCE: 28
gatggttaga gtataatctg taccagatcc actgccactg    40

<210> SEQ ID NO 29
<211> LENGTH: 40
<212> TYPE: DNA
<213> ORGANISM: Homo Sapien

<400> SEQUENCE: 29
gatggagact gggtcatctg gatatcacct ctggcacctg    40

<210> SEQ ID NO 30
<211> LENGTH: 59
<212> TYPE: DNA
<213> ORGANISM: Homo Sapien

<400> SEQUENCE: 30
caaccttgtt gcataataga tcagaagctt aggcgctttc cctggtttct gctggtacc    59

<210> SEQ ID NO 31
<211> LENGTH: 40
<212> TYPE: DNA
<213> ORGANISM: Homo Sapien

-continued

```
<400> SEQUENCE: 31
gatggttaga gtataatctg taccagatcc actgccactg                              40

<210> SEQ ID NO 32
<211> LENGTH: 663
<212> TYPE: PRT
<213> ORGANISM: Homo Sapien

<400> SEQUENCE: 32
```

| | | | | | | | | | | | | | | | |
|---|---|---|---|---|---|---|---|---|---|---|---|---|---|---|---|
| Asp | Ile | Gln | Met | Thr | Gln | Ser | Pro | Ser | Ser | Leu | Ser | Ala | Ser | Val | Gly |
| 1 | | | | 5 | | | | | 10 | | | | | 15 | |
| Asp | Arg | Val | Thr | Ile | Thr | Cys | Lys | Ala | Gly | Gln | Asp | Ile | Lys | Ser | Tyr |
| | | | 20 | | | | | 25 | | | | | 30 | | |
| Leu | Ser | Trp | Tyr | Gln | Gln | Lys | Pro | Gly | Lys | Ala | Pro | Lys | Leu | Leu | Ile |
| | | | 35 | | | | | 40 | | | | | 45 | | |
| Tyr | Tyr | Ala | Thr | Arg | Leu | Ala | Asp | Gly | Val | Pro | Ser | Arg | Phe | Ser | Gly |
| | | 50 | | | | | 55 | | | | | 60 | | | |
| Ser | Gly | Ser | Gly | Thr | Asp | Tyr | Thr | Leu | Thr | Ile | Ser | Ser | Leu | Gln | Pro |
| 65 | | | | | 70 | | | | | 75 | | | | | 80 |
| Glu | Asp | Phe | Ala | Thr | Tyr | Tyr | Cys | Leu | Gln | His | Gly | Glu | Ser | Pro | Trp |
| | | | | 85 | | | | | 90 | | | | | 95 | |
| Thr | Phe | Gly | Gly | Gly | Thr | Lys | Leu | Glu | Ile | Lys | Arg | Thr | Val | Ala | Ala |
| | | | 100 | | | | | 105 | | | | | 110 | | |
| Pro | Ser | Val | Phe | Ile | Phe | Pro | Pro | Ser | Asp | Glu | Gln | Leu | Lys | Ser | Gly |
| | | | 115 | | | | | 120 | | | | | 125 | | |
| Thr | Ala | Ser | Val | Val | Cys | Leu | Leu | Asn | Asn | Phe | Tyr | Pro | Arg | Glu | Ala |
| | | 130 | | | | | 135 | | | | | 140 | | | |
| Lys | Val | Gln | Trp | Lys | Val | Asp | Asn | Ala | Leu | Gln | Ser | Gly | Asn | Ser | Gln |
| 145 | | | | | 150 | | | | | 155 | | | | | 160 |
| Glu | Ser | Val | Thr | Glu | Gln | Asp | Ser | Lys | Asp | Ser | Thr | Tyr | Ser | Leu | Ser |
| | | | | 165 | | | | | 170 | | | | | 175 | |
| Ser | Thr | Leu | Thr | Leu | Ser | Lys | Ala | Asp | Tyr | Glu | Lys | His | Lys | Val | Tyr |
| | | | 180 | | | | | 185 | | | | | 190 | | |
| Ala | Cys | Glu | Val | Thr | His | Gln | Gly | Leu | Ser | Ser | Pro | Val | Thr | Lys | Ser |
| | | | 195 | | | | | 200 | | | | | 205 | | |
| Phe | Asn | Arg | Gly | Glu | Cys | Glu | Val | Gln | Leu | Val | Glu | Ser | Gly | Gly | Gly |
| | | 210 | | | | | 215 | | | | | 220 | | | |
| Leu | Val | Lys | Pro | Gly | Gly | Ser | Leu | Arg | Leu | Ser | Cys | Ala | Ala | Ser | Gly |
| 225 | | | | | 230 | | | | | 235 | | | | | 240 |
| Phe | Thr | Phe | Ser | Asp | Tyr | Tyr | Met | Tyr | Trp | Phe | Arg | Gln | Ala | Pro | Gly |
| | | | | 245 | | | | | 250 | | | | | 255 | |
| Lys | Gly | Leu | Glu | Trp | Val | Ala | Thr | Ile | Ser | Asp | Gly | Gly | Ser | Tyr | Thr |
| | | | 260 | | | | | 265 | | | | | 270 | | |
| Tyr | Tyr | Pro | Asp | Ser | Val | Lys | Gly | Arg | Phe | Thr | Ile | Ser | Arg | Asp | Asn |
| | | | 275 | | | | | 280 | | | | | 285 | | |
| Ala | Lys | Asn | Ser | Leu | Tyr | Leu | Gln | Met | Ser | Ser | Leu | Arg | Ala | Glu | Asp |
| | | 290 | | | | | 295 | | | | | 300 | | | |
| Thr | Ala | Val | Tyr | Tyr | Cys | Ala | Arg | Glu | Glu | Asn | Gly | Asn | Phe | Tyr | Tyr |
| 305 | | | | | 310 | | | | | 315 | | | | | 320 |
| Phe | Asp | Tyr | Trp | Gly | Gln | Gly | Thr | Thr | Val | Thr | Val | Ser | Ser | Ala | Ser |
| | | | | 325 | | | | | 330 | | | | | 335 | |
| Thr | Lys | Gly | Pro | Ser | Val | Phe | Pro | Leu | Ala | Pro | Ser | Ser | Lys | Ser | Thr |
| | | | 340 | | | | | 345 | | | | | 350 | | |

-continued

```
Ser Gly Gly Thr Ala Ala Leu Gly Cys Leu Val Lys Asp Tyr Phe Pro
        355                 360                 365

Glu Pro Val Thr Val Ser Trp Asn Ser Gly Ala Leu Thr Ser Gly Val
370                 375                 380

His Thr Phe Pro Ala Val Leu Gln Ser Ser Gly Leu Tyr Ser Leu Ser
385                 390                 395                 400

Ser Val Val Thr Val Pro Ser Ser Ser Leu Gly Thr Gln Thr Tyr Ile
                405                 410                 415

Cys Asn Val Asn His Lys Pro Ser Asn Thr Lys Val Asp Lys Lys Val
            420                 425                 430

Glu Pro Lys Ser Cys Asp Lys Thr His Thr Cys Pro Pro Cys Pro Ala
        435                 440                 445

Pro Glu Leu Leu Gly Gly Pro Ser Val Phe Leu Phe Pro Pro Lys Pro
    450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
                485                 490                 495

Asp Gly Val Glu Val His Asn Ala Lys Thr Lys Pro Arg Glu Glu Gln
            500                 505                 510

Tyr Asn Ser Thr Tyr Arg Val Val Ser Val Leu Thr Val Leu His Gln
        515                 520                 525

Asp Trp Leu Asn Gly Lys Glu Tyr Lys Cys Lys Val Ser Asn Lys Ala
    530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Asp Glu Leu Thr
                565                 570                 575

Lys Asn Gln Val Ser Leu Thr Cys Leu Val Lys Gly Phe Tyr Pro Ser
            580                 585                 590

Asp Ile Ala Val Glu Trp Glu Ser Asn Gly Gln Pro Glu Asn Asn Tyr
        595                 600                 605

Lys Thr Thr Pro Pro Val Leu Asp Ser Asp Gly Ser Phe Phe Leu Tyr
    610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
                645                 650                 655

Ser Leu Ser Leu Ser Pro Gly
            660

<210> SEQ ID NO 33
<211> LENGTH: 4852
<212> TYPE: PRT
<213> ORGANISM: Homo Sapien

<400> SEQUENCE: 33

Pro Asp Ile Lys Met Thr Gln Ser Pro Ser Ser Met Tyr Ala Ser Leu
1               5                   10                  15

Gly Glu Arg Val Thr Ile Thr Cys Lys Ala Gly Gln Asp Ile Lys Ser
            20                  25                  30

Tyr Leu Ser Trp Tyr Gln Gln Lys Pro Trp Lys Ser Pro Lys Ile Leu
        35                  40                  45

Ile Tyr Tyr Ala Thr Arg Leu Ala Asp Gly Val Pro Ser Arg Phe Ser
    50                  55                  60
```

-continued

```
Gly Ser Gly Ser Gly Gln Asp Tyr Ser Leu Thr Ile Ser Ser Leu Glu
 65                  70                  75                  80

Ser Asp Asp Thr Ala Thr Tyr Tyr Cys Leu Gln His Gly Glu Ser Pro
                 85                  90                  95

Trp Thr Phe Gly Gly Gly Thr Lys Leu Glu Ile Lys Pro Glu Val Gln
            100                 105                 110

Leu Val Glu Ser Gly Gly Gly Leu Val Lys Pro Gly Gly Ser Leu Lys
        115                 120                 125

Leu Ser Cys Ala Ala Ser Gly Phe Thr Phe Ser Asp Tyr Tyr Met Tyr
    130                 135                 140

Trp Phe Arg Gln Thr Pro Glu Lys Arg Leu Glu Trp Val Ala Thr Ile
145                 150                 155                 160

Ser Asp Gly Gly Ser Tyr Thr Tyr Tyr Pro Asp Ser Val Lys Gly Arg
                165                 170                 175

Phe Thr Ile Ser Arg Asp Asn Ala Lys Asn Asn Leu Tyr Leu Gln Met
            180                 185                 190

Ser Ser Leu Lys Ser Glu Asp Thr Ala Met Tyr Tyr Cys Val Arg Glu
        195                 200                 205

Glu Asn Gly Asn Phe Tyr Tyr Phe Asp Tyr Trp Gly Gln Gly Thr Thr
    210                 215                 220

Val Thr Val Ser Ser Asp Gly Ala Thr Ala Thr Ala Ala Gly Ala
225                 230                 235                 240

Thr Gly Ala Cys Cys Ala Gly Thr Cys Thr Cys Ala Thr Cys
                245                 250                 255

Ala Thr Cys Cys Thr Thr Gly Thr Cys Thr Gly Cys Ala Thr Cys Gly
                260                 265                 270

Gly Thr Gly Gly Ala Gly Ala Cys Ala Gly Gly Thr Cys Ala
        275                 280                 285

Cys Thr Ala Thr Cys Ala Cys Thr Thr Gly Cys Ala Ala Gly Gly Cys
    290                 295                 300

Gly Gly Gly Thr Cys Ala Gly Gly Ala Cys Ala Thr Ala Ala Ala
305                 310                 315                 320

Ala Gly Cys Thr Ala Thr Thr Thr Ala Ala Gly Cys Thr Gly Gly Thr
                325                 330                 335

Ala Cys Cys Ala Gly Cys Ala Gly Ala Ala Cys Cys Ala Thr Gly
                340                 345                 350

Gly Ala Ala Ala Gly Cys Gly Cys Thr Ala Ala Gly Ala Thr Cys
        355                 360                 365

Cys Thr Gly Ala Thr Cys Thr Ala Thr Ala Thr Gly Cys Ala Ala
    370                 375                 380

Cys Ala Ala Gly Gly Thr Thr Gly Gly Cys Ala Gly Ala Thr Gly Gly
385                 390                 395                 400

Gly Gly Thr Cys Cys Cys Ala Thr Cys Ala Ala Gly Ala Thr Cys
                405                 410                 415

Ala Gly Thr Gly Gly Cys Ala Gly Thr Gly Gly Ala Thr Cys Thr Gly
            420                 425                 430

Gly Gly Cys Ala Ala Gly Ala Thr Thr Ala Thr Ala Cys Thr Cys Thr
        435                 440                 445

Ala Ala Cys Cys Ala Thr Cys Ala Gly Cys Ala Gly Cys Cys Thr Gly
    450                 455                 460

Cys Ala Gly Cys Cys Thr Gly Ala Gly Gly Ala Thr Thr Thr Cys Gly
465                 470                 475                 480
```

```
Cys Ala Ala Cys Thr Thr Ala Thr Thr Ala Cys Thr Gly Cys Thr
            485                 490                 495
Ala Cys Ala Gly Cys Ala Thr Gly Gly Thr Gly Ala Gly Ala Gly Cys
            500                 505                 510
Cys Cys Gly Thr Gly Gly Ala Cys Gly Thr Thr Cys Gly Gly Thr Gly
            515                 520                 525
Gly Ala Gly Gly Cys Ala Cys Cys Ala Ala Gly Cys Thr Gly Gly Ala
        530                 535                 540
Gly Ala Thr Cys Ala Ala Ala Pro Asp Ile Lys Met Thr Gln Ser Pro
545                 550                 555                 560
Ser Ser Leu Ser Ala Ser Val Gly Asp Arg Val Thr Ile Thr Cys Lys
                565                 570                 575
Ala Gly Gln Asp Ile Lys Ser Tyr Leu Ser Trp Tyr Gln Gln Lys Pro
            580                 585                 590
Trp Lys Ala Pro Lys Ile Leu Ile Tyr Tyr Ala Thr Arg Leu Ala Asp
            595                 600                 605
Gly Val Pro Ser Arg Phe Ser Gly Ser Gly Ser Gly Gln Asp Tyr Thr
        610                 615                 620
Leu Thr Ile Ser Ser Leu Gln Pro Glu Asp Phe Ala Thr Tyr Tyr Cys
625                 630                 635                 640
Leu Gln His Gly Glu Ser Pro Trp Thr Phe Gly Gly Gly Thr Lys Leu
                645                 650                 655
Glu Ile Lys Asp Gly Ala Thr Ala Thr Cys Cys Ala Gly Ala Thr Gly
            660                 665                 670
Ala Cys Cys Cys Ala Gly Thr Cys Thr Cys Cys Ala Thr Cys Ala Thr
        675                 680                 685
Cys Cys Thr Thr Gly Thr Cys Thr Gly Cys Ala Thr Cys Gly Gly Thr
690                 695                 700
Gly Gly Gly Ala Gly Ala Cys Ala Gly Gly Thr Cys Ala Cys Thr
705                 710                 715                 720
Ala Thr Cys Ala Cys Thr Thr Gly Cys Ala Ala Gly Cys Gly Gly
                725                 730                 735
Gly Thr Cys Ala Gly Gly Ala Cys Ala Thr Thr Ala Ala Ala Gly
            740                 745                 750
Cys Thr Ala Thr Thr Thr Ala Ala Gly Cys Thr Gly Gly Thr Ala Cys
            755                 760                 765
Cys Ala Gly Cys Ala Gly Ala Ala Cys Cys Ala Thr Gly Gly Ala
        770                 775                 780
Ala Ala Gly Cys Gly Cys Cys Thr Ala Ala Gly Ala Thr Cys Cys Thr
785                 790                 795                 800
Gly Ala Thr Cys Thr Ala Thr Ala Thr Gly Cys Ala Ala Cys Ala
                805                 810                 815
Ala Gly Gly Thr Thr Gly Gly Cys Ala Gly Ala Thr Gly Gly Gly
            820                 825                 830
Thr Cys Cys Cys Ala Thr Cys Ala Ala Gly Ala Thr Thr Cys Ala Gly
            835                 840                 845
Thr Gly Gly Cys Ala Gly Thr Gly Gly Ala Thr Cys Thr Gly Gly Thr
        850                 855                 860
Ala Cys Ala Gly Ala Thr Thr Ala Thr Ala Cys Thr Cys Thr Ala Ala
865                 870                 875                 880
Cys Cys Ala Thr Cys Ala Gly Cys Ala Gly Cys Cys Thr Gly Cys Ala
                885                 890                 895
```

```
Gly Cys Cys Thr Gly Ala Gly Ala Thr Thr Cys Gly Cys Ala
            900                 905                 910
Ala Cys Thr Thr Ala Thr Ala Cys Thr Gly Thr Cys Thr Ala Cys
            915                 920                 925
Ala Gly Cys Ala Thr Gly Gly Thr Gly Ala Gly Cys Cys Cys
            930                 935                 940
Gly Thr Gly Gly Ala Cys Gly Thr Thr Cys Gly Gly Thr Gly Ala
945                 950                 955                 960
Gly Gly Cys Ala Cys Cys Ala Ala Gly Cys Thr Gly Ala Gly Ala
                965                 970                 975
Thr Cys Ala Ala Ala Pro Asp Ile Gln Met Thr Gln Ser Pro Ser Ser
            980                 985                 990
Leu Ser Ala Ser Val Gly Asp Arg Val Thr Ile Thr Cys Lys Ala Gly
            995                 1000                1005
Gln Asp Ile Lys Ser Tyr Leu Ser Trp Tyr Gln Gln Lys Pro Trp Lys
            1010                1015                1020
Ala Pro Lys Ile Leu Ile Tyr Tyr Ala Thr Arg Leu Ala Asp Gly Val
1025                1030                1035                1040
Pro Ser Arg Phe Ser Gly Ser Gly Ser Gly Thr Asp Tyr Thr Leu Thr
            1045                1050                1055
Ile Ser Ser Leu Gln Pro Glu Asp Phe Ala Thr Tyr Tyr Cys Leu Gln
            1060                1065                1070
His Gly Glu Ser Pro Trp Thr Phe Gly Gly Gly Thr Lys Leu Glu Ile
            1075                1080                1085
Lys Asp Gly Ala Thr Ala Thr Cys Cys Ala Gly Ala Thr Gly Ala Cys
            1090                1095                1100
Cys Cys Ala Gly Thr Cys Thr Cys Cys Ala Thr Cys Ala Thr Cys Cys
1105                1110                1115                1120
Thr Thr Gly Thr Cys Thr Gly Cys Ala Thr Cys Gly Gly Thr Gly Gly
            1125                1130                1135
Gly Ala Gly Ala Cys Ala Gly Gly Thr Cys Ala Cys Thr Ala Thr
            1140                1145                1150
Cys Ala Cys Thr Thr Gly Cys Ala Ala Gly Cys Gly Gly Gly Thr
            1155                1160                1165
Cys Ala Gly Gly Ala Cys Ala Thr Thr Ala Ala Ala Gly Cys Thr
            1170                1175                1180
Ala Thr Thr Thr Ala Ala Gly Cys Thr Gly Gly Thr Ala Cys Cys Ala
1185                1190                1195                1200
Gly Cys Ala Gly Ala Ala Ala Cys Cys Ala Gly Gly Ala Ala Ala
            1205                1210                1215
Gly Cys Gly Cys Cys Thr Ala Ala Gly Cys Cys Thr Cys Thr Gly Ala
            1220                1225                1230
Thr Cys Thr Ala Thr Thr Ala Thr Gly Cys Ala Ala Cys Ala Ala Gly
            1235                1240                1245
Gly Thr Thr Gly Gly Cys Ala Gly Ala Thr Gly Gly Gly Gly Thr Cys
            1250                1255                1260
Cys Cys Ala Thr Cys Ala Ala Gly Ala Thr Thr Cys Ala Gly Thr Gly
1265                1270                1275                1280
Gly Cys Ala Gly Thr Gly Gly Ala Thr Cys Thr Gly Gly Thr Ala Cys
            1285                1290                1295
Ala Gly Ala Thr Thr Ala Thr Ala Cys Thr Cys Thr Ala Ala Cys Cys
            1300                1305                1310
```

```
Ala Thr Cys Ala Gly Cys Ala Gly Cys Cys Thr Gly Cys Ala Gly Cys
            1315                1320                1325
Cys Thr Gly Ala Gly Gly Ala Thr Thr Cys Gly Cys Ala Ala Cys
        1330                1335                1340
Thr Thr Ala Thr Thr Ala Cys Thr Gly Thr Cys Thr Ala Cys Ala Gly
1345                1350                1355                1360
Cys Ala Thr Gly Gly Thr Gly Ala Gly Ala Gly Cys Cys Gly Thr
            1365                1370                1375
Gly Gly Ala Cys Gly Thr Thr Cys Gly Gly Thr Gly Ala Gly Gly
        1380                1385                1390
Cys Ala Cys Cys Ala Ala Gly Cys Thr Gly Gly Ala Gly Ala Thr Cys
    1395                1400                1405
Ala Ala Ala Pro Asp Ile Gln Met Thr Gln Ser Pro Ser Ser Leu Ser
1410                1415                1420
Ala Ser Val Gly Asp Arg Val Thr Ile Thr Cys Lys Ala Gly Gln Asp
1425                1430                1435                1440
Ile Lys Ser Tyr Leu Ser Trp Tyr Gln Gln Lys Pro Gly Lys Ala Pro
            1445                1450                1455
Lys Leu Leu Ile Tyr Tyr Ala Thr Arg Leu Ala Asp Gly Val Pro Ser
        1460                1465                1470
Arg Phe Ser Gly Ser Gly Ser Gly Thr Asp Tyr Thr Leu Thr Ile Ser
        1475                1480                1485
Ser Leu Gln Pro Glu Asp Phe Ala Thr Tyr Tyr Cys Leu Gln His Gly
    1490                1495                1500
Glu Ser Pro Trp Thr Phe Gly Gly Gly Thr Lys Leu Glu Ile Lys Asp
1505                1510                1515                1520
Gly Ala Gly Gly Thr Ala Cys Ala Ala Cys Thr Gly Gly Thr Gly Gly
            1525                1530                1535
Ala Gly Thr Cys Thr Gly Gly Gly Gly Ala Gly Gly Cys Thr Thr
        1540                1545                1550
Ala Gly Thr Gly Ala Ala Gly Cys Cys Thr Gly Gly Ala Gly Gly Gly
        1555                1560                1565
Thr Cys Cys Cys Thr Gly Ala Gly Gly Cys Thr Cys Thr Cys Thr
1570                1575                1580
Gly Thr Gly Cys Ala Gly Cys Cys Thr Cys Thr Gly Gly Ala Thr Thr
1585                1590                1595                1600
Cys Ala Cys Thr Thr Thr Cys Ala Gly Thr Gly Ala Cys Thr Ala Thr
            1605                1610                1615
Thr Ala Cys Ala Thr Gly Thr Ala Thr Thr Gly Gly Thr Thr Thr Cys
        1620                1625                1630
Gly Cys Cys Ala Gly Ala Cys Thr Cys Cys Gly Gly Ala Ala Ala
    1635                1640                1645
Gly Gly Gly Gly Cys Thr Gly Gly Ala Gly Thr Gly Gly Thr Cys
        1650                1655                1660
Gly Cys Ala Ala Cys Cys Ala Thr Thr Ala Gly Thr Gly Ala Thr Gly
1665                1670                1675                1680
Gly Thr Gly Gly Thr Ala Gly Thr Thr Ala Cys Ala Cys Cys Thr Ala
            1685                1690                1695
Cys Thr Ala Thr Cys Cys Ala Gly Ala Cys Ala Gly Thr Gly Thr Gly
        1700                1705                1710
Ala Ala Gly Gly Gly Gly Cys Gly Ala Thr Thr Cys Ala Cys Cys Ala
        1715                1720                1725
```

```
Thr Cys Thr Cys Cys Ala Gly Ala Gly Ala Cys Ala Ala Thr Gly Cys
    1730                1735                1740

Cys Ala Ala Gly Ala Cys Ala Gly Cys Cys Thr Cys Thr Ala Cys
1745                1750                1755                1760

Cys Thr Gly Cys Ala Gly Ala Thr Gly Ala Gly Cys Ala Gly Cys Cys
                1765                1770                1775

Thr Gly Ala Gly Gly Gly Cys Thr Gly Ala Gly Ala Cys Ala Cys
            1780                1785                1790

Ala Gly Cys Cys Ala Thr Gly Thr Ala Thr Ala Cys Thr Gly Thr
        1795                1800                1805

Gly Thr Ala Ala Gly Ala Gly Ala Gly Gly Ala Gly Ala Ala Thr Gly
    1810                1815                1820

Gly Thr Ala Ala Cys Thr Thr Thr Thr Ala Cys Thr Ala Cys Thr Thr
1825                1830                1835                1840

Thr Gly Ala Cys Thr Ala Cys Thr Gly Gly Gly Cys Cys Ala Ala
                1845                1850                1855

Gly Gly Gly Ala Cys Cys Ala Cys Gly Gly Thr Cys Ala Cys Cys Gly
        1860                1865                1870

Thr Cys Thr Cys Cys Thr Cys Ala Pro Glu Val Gln Leu Val Glu Ser
    1875                1880                1885

Gly Gly Gly Leu Val Lys Pro Gly Gly Ser Leu Arg Leu Ser Cys Ala
        1890                1895                1900

Ala Ser Gly Phe Thr Phe Ser Asp Tyr Tyr Met Tyr Trp Phe Arg Gln
1905                1910                1915                1920

Thr Pro Gly Lys Gly Leu Glu Trp Val Ala Thr Ile Ser Asp Gly Gly
                1925                1930                1935

Ser Tyr Thr Tyr Tyr Pro Asp Ser Val Lys Gly Arg Phe Thr Ile Ser
        1940                1945                1950

Arg Asp Asn Ala Lys Asn Ser Leu Tyr Leu Gln Met Ser Ser Leu Arg
            1955                1960                1965

Ala Glu Asp Thr Ala Met Tyr Tyr Cys Val Arg Glu Glu Asn Gly Asn
        1970                1975                1980

Phe Tyr Tyr Phe Asp Tyr Trp Gly Gln Gly Thr Thr Val Thr Val Ser
1985                1990                1995                2000

Ser Asp Gly Ala Gly Gly Thr Ala Cys Ala Ala Cys Thr Gly Gly Thr
        2005                2010                2015

Gly Gly Ala Gly Thr Cys Thr Gly Gly Gly Gly Ala Gly Gly Cys
            2020                2025                2030

Thr Thr Ala Gly Thr Gly Ala Ala Gly Cys Cys Thr Gly Gly Ala Gly
        2035                2040                2045

Gly Gly Thr Cys Cys Cys Thr Gly Ala Gly Gly Cys Thr Cys Thr Cys
    2050                2055                2060

Cys Thr Gly Thr Gly Cys Ala Gly Cys Cys Thr Cys Thr Gly Gly Ala
2065                2070                2075                2080

Thr Thr Cys Ala Cys Thr Thr Thr Cys Ala Gly Thr Gly Ala Cys Thr
            2085                2090                2095

Ala Thr Thr Ala Cys Ala Thr Gly Thr Ala Thr Thr Gly Gly Thr Thr
        2100                2105                2110

Thr Cys Gly Cys Cys Ala Gly Gly Cys Cys Cys Gly Gly Ala
            2115                2120                2125

Ala Ala Gly Gly Gly Gly Cys Thr Gly Gly Ala Gly Thr Gly Gly Gly
        2130                2135                2140
```

```
Thr Cys Gly Cys Ala Ala Cys Cys Ala Thr Ala Gly Thr Gly Ala
2145                2150                2155                2160

Thr Gly Gly Thr Gly Gly Thr Ala Gly Thr Thr Ala Cys Ala Cys
            2165                2170                2175

Thr Ala Cys Thr Ala Thr Cys Cys Ala Gly Ala Cys Ala Gly Thr Gly
        2180                2185                2190

Thr Gly Ala Ala Gly Gly Gly Gly Cys Gly Ala Thr Thr Cys Ala Cys
        2195                2200                2205

Cys Ala Thr Cys Thr Cys Cys Ala Gly Ala Gly Ala Cys Ala Ala Thr
        2210                2215                2220

Gly Cys Cys Ala Ala Gly Ala Ala Cys Ala Gly Cys Cys Thr Cys Thr
2225                2230                2235                2240

Ala Cys Cys Thr Gly Cys Ala Gly Ala Thr Gly Ala Gly Cys Ala Gly
            2245                2250                2255

Cys Cys Thr Gly Ala Gly Gly Gly Cys Thr Gly Ala Gly Gly Ala Cys
            2260                2265                2270

Ala Cys Ala Gly Cys Thr Gly Thr Gly Thr Ala Thr Thr Ala Cys Thr
        2275                2280                2285

Gly Thr Gly Thr Ala Ala Gly Ala Gly Ala Gly Gly Ala Gly Ala Ala
        2290                2295                2300

Thr Gly Gly Thr Ala Ala Cys Thr Thr Thr Ala Cys Thr Ala Cys Thr
2305                2310                2315                2320

Thr Thr Thr Gly Ala Cys Thr Ala Cys Thr Gly Gly Gly Gly Cys Cys
            2325                2330                2335

Ala Ala Gly Gly Gly Ala Cys Cys Ala Cys Gly Gly Thr Cys Ala Cys
            2340                2345                2350

Cys Gly Thr Cys Thr Cys Cys Thr Cys Ala Pro Glu Val Gln Leu Val
        2355                2360                2365

Glu Ser Gly Gly Gly Leu Val Lys Pro Gly Gly Ser Leu Arg Leu Ser
        2370                2375                2380

Cys Ala Ala Ser Gly Phe Thr Phe Ser Asp Tyr Tyr Met Tyr Trp Phe
2385                2390                2395                2400

Arg Gln Ala Pro Gly Lys Gly Leu Glu Trp Val Ala Thr Ile Ser Asp
            2405                2410                2415

Gly Gly Ser Tyr Thr Tyr Tyr Pro Asp Ser Val Lys Gly Arg Phe Thr
            2420                2425                2430

Ile Ser Arg Asp Asn Ala Lys Asn Ser Leu Tyr Leu Gln Met Ser Ser
        2435                2440                2445

Leu Arg Ala Glu Asp Thr Ala Val Tyr Tyr Cys Val Arg Glu Glu Asn
2450                2455                2460

Gly Asn Phe Tyr Tyr Phe Asp Tyr Trp Gly Gln Gly Thr Thr Val Thr
2465                2470                2475                2480

Val Ser Ser Asp Gly Ala Gly Gly Thr Ala Cys Ala Ala Cys Thr Gly
            2485                2490                2495

Gly Thr Gly Gly Ala Gly Thr Cys Thr Gly Gly Gly Gly Gly Ala Gly
            2500                2505                2510

Gly Cys Thr Thr Ala Gly Thr Gly Ala Ala Gly Cys Cys Thr Gly Gly
        2515                2520                2525

Ala Gly Gly Gly Thr Cys Cys Cys Thr Gly Ala Gly Gly Cys Thr Cys
        2530                2535                2540

Thr Cys Cys Thr Gly Thr Gly Cys Ala Gly Cys Cys Thr Cys Thr Gly
2545                2550                2555                2560
```

```
Gly Ala Thr Thr Cys Ala Cys Thr Thr Cys Ala Gly Thr Gly Ala
            2565                2570                2575

Cys Thr Ala Thr Thr Ala Cys Ala Thr Gly Thr Ala Thr Gly Gly
            2580                2585                2590

Thr Thr Thr Cys Gly Cys Cys Ala Gly Gly Cys Cys Cys Gly Gly
            2595                2600                2605

Gly Ala Ala Ala Gly Gly Gly Gly Cys Thr Gly Gly Ala Thr Gly
            2610                2615                2620

Gly Gly Thr Cys Gly Cys Ala Ala Cys Ala Thr Thr Ala Gly Thr
2625                2630                2635                2640

Gly Ala Thr Gly Gly Thr Gly Gly Thr Ala Gly Thr Thr Ala Cys Ala
            2645                2650                2655

Cys Cys Thr Ala Cys Thr Ala Thr Cys Cys Ala Gly Ala Cys Ala Gly
            2660                2665                2670

Thr Gly Thr Gly Ala Ala Gly Gly Gly Cys Gly Ala Thr Thr Cys
            2675                2680                2685

Ala Cys Cys Ala Thr Cys Thr Cys Cys Ala Gly Ala Gly Ala Cys Ala
            2690                2695                2700

Ala Thr Gly Cys Cys Ala Ala Gly Ala Ala Cys Ala Gly Cys Cys Thr
2705                2710                2715                2720

Cys Thr Ala Cys Cys Thr Gly Cys Ala Gly Ala Thr Gly Ala Gly Cys
            2725                2730                2735

Ala Gly Cys Cys Thr Gly Ala Gly Gly Gly Cys Thr Gly Ala Gly Gly
            2740                2745                2750

Ala Cys Ala Cys Ala Gly Cys Thr Gly Thr Gly Thr Ala Thr Thr Ala
            2755                2760                2765

Cys Thr Gly Thr Gly Thr Ala Ala Gly Ala Gly Ala Gly Gly Ala Gly
            2770                2775                2780

Ala Ala Thr Gly Gly Thr Ala Ala Cys Thr Thr Thr Ala Cys Thr
2785                2790                2795                2800

Ala Cys Thr Thr Thr Gly Ala Cys Thr Ala Cys Thr Gly Gly Gly Gly
            2805                2810                2815

Cys Cys Ala Ala Gly Gly Gly Ala Cys Cys Ala Cys Gly Thr Cys
            2820                2825                2830

Ala Cys Cys Gly Thr Cys Thr Cys Cys Thr Cys Ala Pro Glu Val Gln
            2835                2840                2845

Leu Val Glu Ser Gly Gly Gly Leu Val Lys Pro Gly Gly Ser Leu Arg
            2850                2855                2860

Leu Ser Cys Ala Ala Ser Gly Phe Thr Phe Ser Asp Tyr Tyr Met Tyr
2865                2870                2875                2880

Trp Val Arg Gln Ala Pro Gly Lys Gly Leu Glu Trp Val Ala Thr Ile
            2885                2890                2895

Ser Asp Gly Gly Ser Tyr Thr Tyr Tyr Pro Asp Ser Val Lys Gly Arg
            2900                2905                2910

Phe Thr Ile Ser Arg Asp Asn Ala Lys Asn Ser Leu Tyr Leu Gln Met
            2915                2920                2925

Ser Ser Leu Arg Ala Glu Asp Thr Ala Val Tyr Tyr Cys Ala Arg Glu
            2930                2935                2940

Glu Asn Gly Asn Phe Tyr Tyr Phe Asp Tyr Trp Gly Gln Gly Thr Thr
2945                2950                2955                2960

Val Thr Val Ser Ser Asp Gly Ala Gly Gly Thr Ala Cys Ala Ala Cys
            2965                2970                2975
```

-continued

```
Thr Gly Gly Thr Gly Gly Ala Gly Thr Cys Thr Gly Gly Gly Gly
        2980            2985            2990

Ala Gly Gly Cys Thr Thr Ala Gly Thr Gly Ala Ala Gly Cys Cys Thr
        2995            3000            3005

Gly Gly Ala Gly Gly Thr Cys Cys Cys Thr Gly Ala Gly Gly Cys
        3010            3015            3020

Thr Cys Thr Cys Cys Thr Gly Thr Gly Cys Ala Gly Cys Cys Thr Cys
3025            3030            3035            3040

Thr Gly Gly Ala Thr Thr Cys Ala Cys Thr Thr Thr Cys Ala Gly Thr
        3045            3050            3055

Gly Ala Cys Thr Ala Thr Thr Ala Cys Ala Thr Gly Thr Ala Thr Thr
        3060            3065            3070

Gly Gly Thr Thr Thr Cys Gly Cys Cys Ala Gly Gly Cys Cys Cys Cys
        3075            3080            3085

Gly Gly Gly Ala Ala Ala Gly Gly Gly Cys Thr Gly Gly Ala Gly
        3090            3095            3100

Thr Gly Gly Gly Thr Cys Gly Cys Ala Ala Cys Cys Ala Thr Thr Ala
3105            3110            3115            3120

Gly Thr Gly Ala Thr Gly Gly Thr Gly Gly Thr Ala Gly Thr Thr Ala
        3125            3130            3135

Cys Ala Cys Cys Thr Ala Cys Thr Ala Thr Cys Cys Ala Gly Ala Cys
        3140            3145            3150

Ala Gly Thr Gly Thr Gly Ala Ala Gly Gly Gly Gly Cys Gly Ala Thr
        3155            3160            3165

Thr Cys Ala Cys Cys Ala Thr Cys Thr Cys Cys Ala Gly Ala Gly Ala
        3170            3175            3180

Cys Ala Ala Thr Gly Cys Cys Ala Ala Gly Ala Ala Cys Ala Gly Cys
3185            3190            3195            3200

Cys Thr Cys Thr Ala Cys Cys Thr Gly Cys Ala Gly Ala Thr Gly Ala
        3205            3210            3215

Gly Cys Ala Gly Cys Cys Thr Gly Ala Gly Gly Cys Thr Gly Ala
        3220            3225            3230

Gly Gly Ala Cys Ala Cys Ala Gly Cys Thr Gly Thr Gly Thr Ala Thr
        3235            3240            3245

Thr Ala Cys Thr Gly Cys Gly Cys Ala Ala Gly Ala Gly Ala Gly Gly
3250            3255            3260

Ala Gly Ala Ala Thr Gly Gly Thr Ala Ala Cys Thr Thr Thr Ala
3265            3270            3275            3280

Cys Thr Ala Cys Thr Thr Thr Gly Ala Cys Thr Ala Cys Thr Gly Gly
        3285            3290            3295

Gly Gly Cys Cys Ala Ala Gly Gly Ala Cys Cys Ala Cys Gly Gly
        3300            3305            3310

Thr Cys Ala Cys Cys Gly Thr Cys Thr Cys Cys Thr Cys Ala Pro Glu
        3315            3320            3325

Val Gln Leu Val Glu Ser Gly Gly Gly Leu Val Lys Pro Gly Gly Ser
        3330            3335            3340

Leu Arg Leu Ser Cys Ala Ala Ser Gly Phe Thr Phe Ser Asp Tyr Tyr
3345            3350            3355            3360

Met Tyr Trp Phe Arg Gln Ala Pro Gly Lys Gly Leu Glu Trp Val Ala
        3365            3370            3375

Thr Ile Ser Asp Gly Gly Ser Tyr Thr Tyr Tyr Pro Asp Ser Val Lys
        3380            3385            3390
```

-continued

```
Gly Arg Phe Thr Ile Ser Arg Asp Asn Ala Lys Asn Ser Leu Tyr Leu
        3395                3400                3405

Gln Met Ser Ser Leu Arg Ala Glu Asp Thr Ala Val Tyr Tyr Cys Ala
    3410                3415                3420

Arg Glu Glu Asn Gly Asn Phe Tyr Tyr Phe Asp Tyr Trp Gly Gln Gly
3425                3430                3435                3440

Thr Thr Val Thr Val Ser Ser Asp Gly Cys Cys Thr Gly Gly Ala Gly
            3445                3450                3455

Gly Gly Thr Cys Cys Cys Thr Gly Ala Gly Gly Cys Thr Cys Thr Cys
            3460                3465                3470

Cys Thr Gly Thr Gly Cys Ala Gly Cys Thr Cys Ser Glu Gln Asp
        3475                3480                3485

Gly Thr Thr Thr Cys Gly Cys Cys Ala Gly Ala Cys Thr Cys Cys Gly
    3490                3495                3500

Gly Gly Ala Ala Gly Gly Gly Gly Cys Thr Gly Gly Ala Gly Thr
3505                3510                3515                3520

Gly Gly Gly Thr Cys Gly Cys Ala Ala Cys Ser Glu Gln Asp Cys Ala
            3525                3530                3535

Gly Ala Gly Ala Cys Ala Ala Thr Gly Cys Cys Ala Ala Gly Ala Ala
            3540                3545                3550

Cys Ala Gly Cys Cys Thr Cys Thr Ala Cys Cys Thr Gly Cys Ala Gly
        3555                3560                3565

Ala Thr Gly Ala Gly Cys Ala Gly Cys Cys Thr Gly Ala Gly Gly Gly
        3570                3575                3580

Cys Thr Gly Ala Gly Gly Ala Cys Ala Cys Gly Cys Cys Ala Thr
3585                3590                3595                3600

Gly Asp Cys Ala Thr Gly Thr Ala Thr Thr Gly Gly Thr Thr Thr Cys
            3605                3610                3615

Gly Cys Cys Ala Gly Cys Cys Cys Cys Gly Gly Gly Ala Ala Ala
        3620                3625                3630

Gly Gly Gly Gly Cys Thr Gly Gly Asp Gly Gly Gly Cys Thr Gly Ala
            3635                3640                3645

Gly Gly Ala Cys Ala Cys Ala Gly Cys Thr Gly Thr Gly Thr Ala Thr
        3650                3655                3660

Thr Ala Cys Thr Gly Thr Gly Thr Ala Ala Gly Ala Gly Asp Gly Thr
3665                3670                3675                3680

Gly Ala Cys Thr Ala Thr Ala Cys Ala Thr Gly Thr Ala Thr Thr
            3685                3690                3695

Gly Gly Gly Thr Gly Cys Gly Cys Cys Ala Gly Gly Cys Cys Cys Cys
        3700                3705                3710

Gly Gly Gly Ala Ala Ala Gly Gly Gly Gly Cys Thr Gly Gly Ala Gly
            3715                3720                3725

Asp Gly Ala Gly Gly Gly Cys Thr Gly Ala Gly Gly Ala Cys Ala Cys
            3730                3735                3740

Ala Gly Cys Thr Gly Thr Gly Thr Ala Thr Thr Ala Cys Thr Gly Cys
3745                3750                3755                3760

Gly Cys Ala Ala Gly Ala Gly Ala Gly Ala Gly Ala Ala Thr Gly
        3765                3770                3775

Gly Thr Ala Ala Cys Asp Cys Thr Thr Gly Cys Ala Ala Gly Thr Gly
            3780                3785                3790

Ala Thr Ala Gly Thr Gly Ala Cys Cys Cys Thr Gly Thr Cys Thr Cys
3795                3800                3805
```

-continued

```
Cys Cys Ala Cys Cys Gly Ala Thr Gly Cys Ala Gly Ala Cys Ala Ala
    3810                3815                3820

Gly Gly Ala Thr Gly Ala Thr Gly Gly Ala Gly Ala Cys Thr Gly Gly
3825                3830                3835                3840

Gly Thr Cys Ala Thr Cys Asp Cys Ala Thr Ala Thr Ala Gly Ala
            3845                3850                3855

Thr Cys Ala Gly Gly Ala Thr Cys Thr Thr Ala Gly Gly Cys Gly Cys
                3860                3865                3870

Thr Thr Thr Cys Cys Ala Thr Gly Gly Thr Thr Thr Cys Thr Gly Cys
        3875                3880                3885

Thr Gly Asp Gly Thr Ala Gly Ala Cys Ala Gly Thr Ala Ala Thr Ala
    3890                3895                3900

Ala Gly Thr Thr Gly Cys Gly Ala Ala Ala Thr Cys Cys Thr Cys Ala
3905                3910                3915                3920

Gly Gly Cys Thr Gly Cys Ala Gly Gly Cys Thr Gly Cys Thr Gly Ala
            3925                3930                3935

Thr Gly Gly Thr Thr Ala Gly Ala Gly Thr Ala Thr Ala Ala Thr Cys
                3940                3945                3950

Thr Thr Gly Cys Cys Cys Ala Gly Ala Thr Cys Asp Gly Ala Thr Gly
        3955                3960                3965

Gly Ala Gly Ala Cys Thr Gly Gly Gly Thr Cys Ala Thr Cys Thr Gly
    3970                3975                3980

Gly Ala Thr Ala Thr Cys Ala Cys Cys Thr Thr Gly Gly Cys Ala
3985                3990                3995                4000

Cys Cys Thr Gly Asp Gly Ala Thr Gly Gly Thr Thr Ala Gly Ala Gly
            4005                4010                4015

Thr Ala Thr Ala Ala Thr Cys Thr Gly Thr Ala Cys Cys Ala Gly Ala
                4020                4025                4030

Thr Cys Cys Ala Cys Thr Gly Cys Cys Ala Cys Thr Gly Asp Gly Ala
        4035                4040                4045

Thr Gly Gly Ala Gly Ala Cys Thr Gly Gly Gly Thr Cys Ala Thr Cys
    4050                4055                4060

Thr Gly Gly Ala Thr Ala Thr Cys Ala Cys Cys Thr Cys Thr Gly Gly
4065                4070                4075                4080

Cys Ala Cys Cys Thr Gly Asp Cys Ala Ala Cys Cys Thr Thr Gly Thr
            4085                4090                4095

Thr Gly Cys Ala Thr Ala Ala Thr Ala Gly Ala Thr Cys Ala Gly Ala
                4100                4105                4110

Ala Gly Cys Thr Thr Ala Gly Gly Cys Gly Cys Thr Thr Thr Cys Cys
        4115                4120                4125

Cys Thr Gly Gly Thr Thr Thr Cys Thr Gly Cys Thr Gly Gly Thr Ala
    4130                4135                4140

Cys Cys Asp Gly Ala Thr Gly Gly Thr Thr Ala Gly Ala Gly Thr Ala
4145                4150                4155                4160

Thr Ala Ala Thr Cys Thr Gly Thr Ala Cys Cys Ala Gly Ala Thr Cys
            4165                4170                4175

Cys Ala Cys Thr Gly Cys Cys Ala Cys Thr Gly Pro Asp Ile Gln Met
                4180                4185                4190

Thr Gln Ser Pro Ser Ser Leu Ser Ala Ser Val Gly Asp Arg Val Thr
        4195                4200                4205

Ile Thr Cys Lys Ala Gly Gln Asp Ile Lys Ser Tyr Leu Ser Trp Tyr
    4210                4215                4220
```

-continued

```
Gln Gln Lys Pro Gly Lys Ala Pro Lys Leu Leu Ile Tyr Tyr Ala Thr
4225                4230                4235                4240

Arg Leu Ala Asp Gly Val Pro Ser Arg Phe Ser Gly Ser Gly Ser Gly
                4245                4250                4255

Thr Asp Tyr Thr Leu Thr Ile Ser Ser Leu Gln Pro Glu Asp Phe Ala
            4260                4265                4270

Thr Tyr Tyr Cys Leu Gln His Gly Glu Ser Pro Trp Thr Phe Gly Gly
        4275                4280                4285

Gly Thr Lys Leu Glu Ile Lys Arg Thr Val Ala Ala Pro Ser Val Phe
    4290                4295                4300

Ile Phe Pro Pro Ser Asp Glu Gln Leu Lys Ser Gly Thr Ala Ser Val
4305                4310                4315                4320

Val Cys Leu Leu Asn Asn Phe Tyr Pro Arg Glu Ala Lys Val Gln Trp
                4325                4330                4335

Lys Val Asp Asn Ala Leu Gln Ser Gly Asn Ser Gln Glu Ser Val Thr
            4340                4345                4350

Glu Gln Asp Ser Lys Asp Ser Thr Tyr Ser Leu Ser Ser Thr Leu Thr
        4355                4360                4365

Leu Ser Lys Ala Asp Tyr Glu Lys His Lys Val Tyr Ala Cys Glu Val
    4370                4375                4380

Thr His Gln Gly Leu Ser Ser Pro Val Thr Lys Ser Phe Asn Arg Gly
4385                4390                4395                4400

Glu Cys Pro Glu Val Gln Leu Val Glu Ser Gly Gly Gly Leu Val Lys
                4405                4410                4415

Pro Gly Gly Ser Leu Arg Leu Ser Cys Ala Ala Ser Gly Phe Thr Phe
            4420                4425                4430

Ser Asp Tyr Tyr Met Tyr Trp Phe Arg Gln Ala Pro Gly Lys Gly Leu
        4435                4440                4445

Glu Trp Val Ala Thr Ile Ser Asp Gly Gly Ser Tyr Thr Tyr Tyr Pro
    4450                4455                4460

Asp Ser Val Lys Gly Arg Phe Thr Ile Ser Arg Asp Asn Ala Lys Asn
4465                4470                4475                4480

Ser Leu Tyr Leu Gln Met Ser Ser Leu Arg Ala Glu Asp Thr Ala Val
                4485                4490                4495

Tyr Tyr Cys Ala Arg Glu Glu Asn Gly Asn Phe Tyr Tyr Phe Asp Tyr
            4500                4505                4510

Trp Gly Gln Gly Thr Thr Val Thr Val Ser Ser Ala Ser Thr Lys Gly
        4515                4520                4525

Pro Ser Val Phe Pro Leu Ala Pro Ser Ser Lys Ser Thr Ser Gly Gly
    4530                4535                4540

Thr Ala Ala Leu Gly Cys Leu Val Lys Asp Tyr Phe Pro Glu Pro Val
4545                4550                4555                4560

Thr Val Ser Trp Asn Ser Gly Ala Leu Thr Ser Gly Val His Thr Phe
                4565                4570                4575

Pro Ala Val Leu Gln Ser Ser Gly Leu Tyr Ser Leu Ser Ser Val Val
            4580                4585                4590

Thr Val Pro Ser Ser Ser Leu Gly Thr Gln Thr Tyr Ile Cys Asn Val
        4595                4600                4605

Asn His Lys Pro Ser Asn Thr Lys Val Asp Lys Lys Val Glu Pro Lys
    4610                4615                4620

Ser Cys Asp Lys Thr His Thr Cys Pro Pro Cys Pro Ala Pro Glu Leu
4625                4630                4635                4640
```

-continued

```
Leu Gly Gly Pro Ser Val Phe Leu Phe Pro Pro Lys Pro Lys Asp Thr
            4645                4650            4655

Leu Met Ile Ser Arg Thr Pro Glu Val Thr Cys Val Val Val Asp Val
        4660            4665            4670

Ser His Glu Asp Pro Glu Val Lys Phe Asn Trp Tyr Val Asp Gly Val
    4675            4680            4685

Glu Val His Asn Ala Lys Thr Lys Pro Arg Glu Glu Gln Tyr Asn Ser
    4690            4695            4700

Thr Tyr Arg Val Val Ser Val Leu Thr Val Leu His Gln Asp Trp Leu
4705            4710            4715            4720

Asn Gly Lys Glu Tyr Lys Cys Lys Val Ser Asn Lys Ala Leu Pro Ala
                4725            4730            4735

Pro Ile Glu Lys Thr Ile Ser Lys Ala Lys Gly Gln Pro Arg Glu Pro
            4740            4745            4750

Gln Val Tyr Thr Leu Pro Pro Ser Arg Asp Glu Leu Thr Lys Asn Gln
        4755            4760            4765

Val Ser Leu Thr Cys Leu Val Lys Gly Phe Tyr Pro Ser Asp Ile Ala
    4770            4775            4780

Val Glu Trp Glu Ser Asn Gly Gln Pro Glu Asn Asn Tyr Lys Thr Thr
4785            4790            4795            4800

Pro Pro Val Leu Asp Ser Asp Gly Ser Phe Phe Leu Tyr Ser Lys Leu
            4805            4810            4815

Thr Val Asp Lys Ser Arg Trp Gln Gln Gly Asn Val Phe Ser Cys Ser
                4820            4825            4830

Val Met His Glu Ala Leu His Asn His Tyr Thr Gln Lys Ser Leu Ser
        4835            4840            4845

Leu Ser Pro Gly
    4850
```

US 7,429,644 B2

HUMANIZED ANTI-LT-β-R ANTIBODIES

RELATED APPLICATIONS

This application is a continuation of International Application No. PCT/US01/32140 filed on Oct. 12, 2001 which claims benefit of U.S. Provisional Application No. 60/299,987 filed on June 21, 2001, U.S. Provisional Application No. 60/275,289, filed on March 13, 2001, and U.S. Provisional Application No. 60/240,285, filed on Oct. 13, 2000. The entire disclosure of each of the aforesaid patent applications are incorporated herein by reference.

FIELD OF THE INVENTION

This invention relates generally to humanized antibodies specific for the lymph toxin beta receptor (LT-β-R).

BACKGROUND OF THE INVENTION

Lymph toxin beta receptor (referred to herein as LT-β-R) is a member of the tumor necrosis factor family which has a well-described role both in the development of the immune system and in the functional maintenance of a number of cells in the immune system including follicular dendrite cells and a number of stoma cell types (Matsumoto et al., *Immune. Rev.* 156:137 (1997). Known legends to the LT-β-R include LTα1/β2 and a second legend called LIGHT (Mauri et al. *Immunity* 8:21 (1998)). Activation of LT-β-R has been shown to induce the apoptotic death of certain cancer cell lines in vivo (PCT/US96/01386). Treatment with agonist LT-β-R activating agents, such as specific humanized anti-LT-β-R antibodies, would thus be useful for treating or reducing the advancement, severity or effects of neoclassic in subjects (e.g., humans).

SUMMARY OF THE INVENTION

The present invention provides humanized anti-lymph toxin beta receptor (LT-β-R) antibodies and methods of using these antibodies to treat or reduce the advancement, severity or effects of neoclassic in subjects (e.g., humans).

Specifically, the invention embraces a humanized antibody that specifically binds to LT-β-R (e.g., human LT-β-R). This antibody comprises light chain complementary determining regions defined by amino acid residues 24 to 34, 50 to 56 and 89 to 97 of SEQ ID NO:1, and/or heavy chain complementary determining regions defined by amino acid residues 31 to 35, 50 to 66 and 99 to 109 of SEQ ID NO:2 and in addition at least one (e.g., 1, 2, 3, 4, or 5) of the following residues in its light chain: K3, W41, I46, Q69 and Y71; or at least one (e.g. 1, 2, 3, 4, or 5) of the following residues in its heavy chain: F37, T40, A49, M89 and V93 (Kabat numbering convention).

The humanized antibody of this invention may comprise a light chain variable domain sequence defined by amino acid residues 1 to 107 of SEQ ID NO:8 and/or a heavy chain variable domain sequence defined by amino acid residues 1 to 120 of SEQ ID NO:16. The humanized antibody may also comprise the same heavy and/or light chain polypeptide sequences as an antibody produced by cell line E46.4 (ATCC patent deposit designation PTA-3357) or cell line E77.4 (ATCC patent deposit designation 3765).

In another embodiment, the humanized antibody of this invention substantially retains the binding properties of the parent antibody. In one embodiment the humanized antibody of this invention binds to LT-β-R with a functional affinity, for instance, of about 1 pM to about 10 pM, alternatively, about 10 pM to about 20 pM, alternatively, about 20 pM to about 30 pM, alternatively, about 30 pM to about 40 pM alternatively, about 40 pM to about 50 pM, alternatively, about 50 pM to about 60 pM, alternatively, about 60 pM to about 70 pM, alternatively, about 70 pM to about 80 pM, and alternatively, about 80 pM to about 90 pM, wherein the functional affinity is measured by FACS in accordance with Example 8.

In another embodiment, the humanized antibody of this invention is linked to an immunologic (e.g., racing A chain and *Pseudomonas toxin*). The humanized antibody of this invention can also be linked to a chemotherapeutic drug (e.g., Adriamycin, 5FU, Vinblastine, Actinomycin D, Topside, Capsulation, Methotrexate and Doxorubicin) or to a radioisotope. The present invention also embraces a combination therapy in which for instance, the humanized antibody of the present invention which is linked to an immunologic is used in combination with a humanized antibody of the present invention which is linked to a chemotherapeutic drug. The present invention further embraces a composition suitable for administration to a mammal (ie human) having a tumor that over expresses LTβR comprising a) a humanized anti-LTβR antibody either alone or linked to a immunologic or a chemotherapeutic drug and b) a catatonic factor, each present in amounts effective to reduce tumor volume upon administration to the mammal. The catatonic factor may include for instance, TNF-α, TNF-β, IL-1, INF-γ, IL-2. Alternatively, the catatonic factor may by a chemotherapeutic drug. The chemotherapeutic drug may include for instance, Adriamycin, 5FU, Vinblastine, Actinomycin D, Topside, Capsulation, Methotrexate and Doxorubicin.

The antibody of this invention can be, for instance, a whole antibody (i.e. with two full length light chains and two full length heavy chains) of any isotype and subtypes (e.g. IgM, IgD, IgG1, IgG2, IgG3, IgG4, IgE, IgA1 and IgA2); alternatively, it can be an antigen-binding fragment (e.g., Fab, F(ab')$_2$, and Fv) of a whole antibody. Embraced in this invention are also a composition comprising a pharmaceutically acceptable carrier; an isolated nucleic acid comprising a coding sequence for SEQ ID NO:8; an isolated nucleic acid comprising a coding sequence for SEQ ID NO:16; an isolated nucleic acid comprising a coding sequence for the light chain of an antibody produced by cell line E46.4 (ATCC patent deposit designation PTA-3357) or cell line E77.4 (ATCC patent deposit designation 3765); an isolated nucleic acid comprising a coding sequence for the heavy chain of an antibody produced by cell line E46.4 (ATCC patent deposit designation PTA-3357) or cell line E77.4 (ATCC patent deposit designation 3765); an isolated nucleic acid comprising a coding sequence for residues 1-107 of SEQ ID NO:8; and an isolated nucleic acid comprising a coding sequence for residues 1-120 of SEQ ID NO:16.

Embraced within the present invention are also cells from cell lines that produce humanized anti-LTβR antibody, included, for instance, cell line E46.4 (ATCC patent deposit designation PTA-3357) and cell line E77.4 (ATCC patent deposit designation 3765). In one embodiment the cell line produces from about 250 mg/L to about 300 mg/L of said antibody, alternatively, the cell line produces from about 300 mg/L to about 350 mg/L of said antibody, alternatively, the cell line produces from about 350 mg/L to about 400 mg/L of said antibody, alternatively, the cell line produces from about 400 mg/L to about 450 mg/L of said antibody, alternatively, the cell line produces from about 450 mg/L to about 500 mg/L of said antibody, alternatively, the cell line produces from about 500 mg/L to about 550 mg/L of said antibody and alternatively, the cell line produces from about 550 mg/L to about 600 mg/L of said antibody. The concentration of the antibody produced by the cell lines is measures as a harvest titer from a 10 day fed batch culture.

The present invention also provides a method of treating or reducing the advancement, severity or effects of neoclassic in a subject (e.g., human) comprising administering to the subject an effective amount of an antibody of this invention. An effective amount of the composition can be administered in one or more dosages. In another embodiment the present invention provides a method of treating or reducing the advancement, severity or effects of neoclassic in a subject (e.g., human) comprising administering to the subject an effective amount of an antibody of this invention and a catatonic factor. The catatonic factor may include for instance, TNF-α, TNF-β, IL-1, INF-γ, IL-2. Alternatively, the catatonic factor may by a chemotherapeutic drug. The chemotherapeutic drug may include for instance, Adriamycin, 5FU, Vinblastine, Actinomycin D, Topside, Capsulation, Methotrexate and Doxorubicin.

BRIEF DESCRIPTION OF THE DRAWINGS

FIG. 1A shows captured mCBE11 (murine) (diamond), captured huCBE11#2 (humanized anti-LT-β-R antibody comprising version 2 of the light chain (VL#2) and version 2 of the heavy chain(VH#2)) (circle), captured huCBE11#4 (humanized anti-LT-β-R antibody comprising version 3 of the light chain (VL#3) and version 4 of the heavy chain (VH#4)) (star). FIG. 1B shows captured mCBE11 (murine) (diamond), captured huCBE11#2 (humanized anti-LT-β-R antibody comprising version 2 of the light chain (VL#2) and version 2 of the heavy chain(VH#2)) (circle), captured huCBE11#4 (humanized anti-LT-β-R antibody comprising version 3 of the light chain (VL#3) and version 4 of the heavy chain (VH#4)) (star).

FIGS. 2A and 2B show graphs of IL-8 agonism on A375 cells. FIG. 1A shows mCBEI 11 (diamonds), captured huCBE11#2 (humanized anti-LT-β-R antibody comprising version 2 of the light chain (VL#2) and version 2 of the heavy chain(VH#2)) (circle), and captured huCBE11#4 (humanized anti-LT-β-R antibody comprising version 3 of the light chain (VL#3) and version 4 of the heavy chain (VH#4)) (stars). FIG. 2B shows captured mCBE11 (diamonds), huCBE11#2 (humanized anti-LT-β-R antibody comprising version 2 of the light chain (VL#2) and version 2 of the heavy chain (VH#2)) (circle), and huCBE11 #4 (humanized anti-LT-13-R antibody comprising version 3 of the light chain (VL#3) and version 4 of the heavy chain (VH#4)) (stars).

DETAILED DESCRIPTION

Sequence Identification Numbers

Figure 1A:
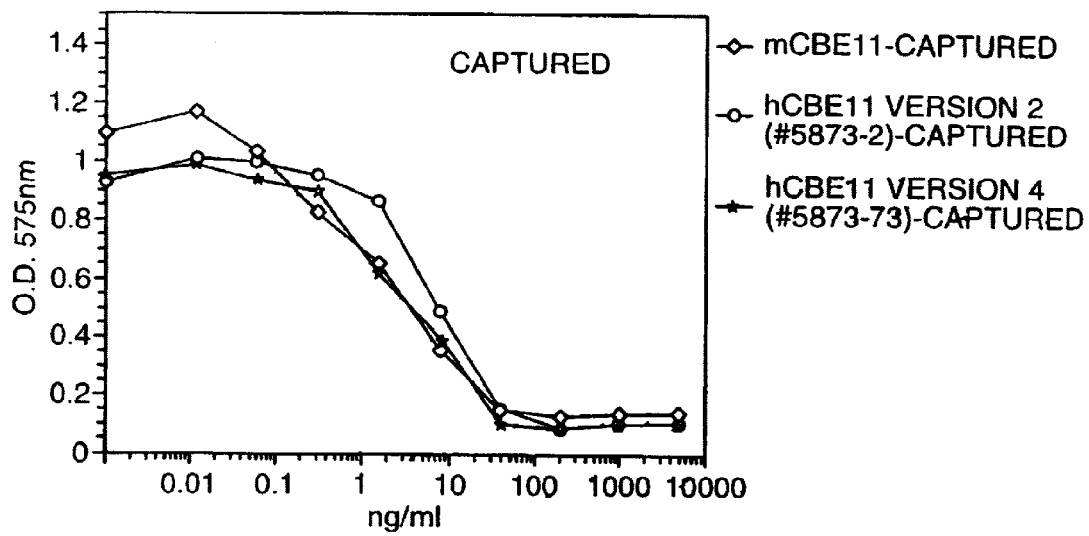
FIGS. 1A and 1B show graphs of cytotoxicity on WiDr cells.

Nucleotide and amino acid sequences referred to in the specification have been given the following sequence identification numbers:

SEQ ID NO: 1—Amino acid sequence of mCBE11 heavy chain variable region.

SEQ ID NO: 2—Amino acid sequence of mCBE11 light chain variable domain.

SEQ ID NO: 3—Nucleic acid sequence of humanized CBE11 light chain variable region (version 1-VL# 1).

SEQ ID NO: 4—Amino acid sequence of humanized CBE11 light chain variable region (version 1-VL#1).

SEQ ID NO: 5—Nucleic acid sequence of humanized CBE11 light chain variable region (version 2-VL#2).

SEQ ID NO: 6—Amino acid sequence of humanized CBE11 light chain variable region (version 2-VL#2)

SEQ ID NO: 7—Nucleic acid sequence of humanized CBE11 light chain variable region (version 3-VL#3).

SEQ ID NO: 8—Amino acid sequence of humanized CBE11 light chain variable region (version 3-VL#3)

SEQ ID NO: 9—Nucleic acid sequence of humanized CBE11 heavy chain variable region (version 1-VH# 1)

SEQ ID NO: 10—Amino acid sequence of humanized CBE11 light chain variable region (version 1-VH# 1)

SEQ ID NO: 11—Nucleic acid sequence of humanized CBE11 heavy chain variable region (version 2-VH#2)

SEQ ID NO: 12—Amino acid sequence of humanized CBE11 light chain variable region (version 2-VH#2)

SEQ ID NO: 13—Nucleic acid sequence of humanized CBE11 heavy chain variable region (version 3-VH#3)

SEQ ID NO: 14—Amino acid sequence of humanized CBE11 light chain variable region (version 3-VH#3)

SEQ ID NO: 15—Nucleic acid sequence of humanized CBE11 heavy chain variable region (version 4-VH#4)

SEQ ID NO: 16—Amino acid sequence of humanized CBE11 heavy chain variable chain region (version 4-VH#4)

SEQ ID NO: 17—FR1 primer to introduce a Bsu36I site.

SEQ ID NO: 18—FR2 primer to introduce Nice and Haiti sites.

SEQ ID NO: 19—FR3 primer to introduce Bsu36I and Pits sites.

SEQ ID NO: 20—FR2 primer to introduce Sami site.

SEQ ID NO: 21—FR3 primer to introduce Put site.

SEQ ID NO: 22—FR2 primer to introduce Sami and Hay sites.

SEQ ID NO: 23—FR3 primer to introduce PvuII and FspI sites.

SEQ ID NO: 24—FR1 primer to introduce HinfI and NsiI sites.

SEQ ID NO: 25—FR2 primer to introduce HaeII and HhaI sites.

SEQ ID NO: 26—FR3 primer to introduce Bsu36I, DdeI and PstI sites.
SEQ ID NO: 27—FR1 primer to introduce EcoRV site.
SEQ ID NO: 28—FR3 primer to introduce RsaI site.
SEQ ID NO: 29—FR1 primer to introduce EcoRV site.
SEQ ID NO: 30—FR2 primer to introduce HindIII site.
SEQ ID NO: 31—FR3 primer to introduce RsaI site.
SEQ ID NO: 32—Full huCBE11 light chain (version 3) including constant domain.
SEQ ID NO: 33—Full huCBE11 heavy chain (version 4) including constant domain.

Definitions

The term humanized antibody, as used herein, refers to herein an antibody derived from a non-human antibody, typically murine, that retains or substantially retains the antigen-binding properties of the parent antibody but which is less immunogenic in humans.

The term complementarily determining region (CDR), as used herein, refers to amino acid sequences which together define the binding affinity and specificity of the natural Fv region of a native immunoglobulin binding site as delineated by Kabat et al (1991).

The term framework region (FR), as used herein, refers to amino acid sequences interposed between CDRs. These portions of the antibody serve to hold the CDRs in appropriate orientation (allows for CDRs to bind antigen).

The term constant region (CR) as used herein, refers to the portion of the antibody molecule which confers effectors functions. In the present invention, murine constant regions are substituted by human constant regions. The constant regions of the subject chimerical or humanized antibodies are derived from human immunoglobulin's. The heavy chain constant region can be selected from any of the five isotopes: alpha, delta, epsilon, gamma or mu. Further, heavy chains of various subclasses (such as the IgG subclasses of heavy chains) are responsible for different effectors functions and thus, by choosing the desired heavy chain constant region, antibodies with desired effectors function can be produced. Preferred constant regions are gamma 1 (IgG1), gamma 3 (IgG3) and gamma 4 (IgG4). More preferred is an Fc region of the gamma 1 (IgG1) isotope. The light chain constant region can be of the kappa or lambda type, preferably of the kappa type.

The term chimerical antibody as used herein refers to an antibody containing sequences derived from two different antibodies, which typically are of different species. Most typically chimerical antibodies comprise human and murine antibody fragments, generally human constant and murine variable region.

The term immunogenicity as used herein refers to a measure of the ability of a targeting protein or therapeutic moiety to elicit an immune response (humeral or cellular) when administered to a recipient. The present invention is concerned with the immunogenicity of the subject humanized antibodies.

Humanized antibody of reduced immunogenicity refers to a humanized antibody exhibiting reduced immunogenicity relative to the parent antibody, e.g., the murine antibody.

Humanized antibody substantially retaining the binding properties of the parent antibody refers to a humanized antibody which retains the ability to specifically bind the antigen recognized by the parent antibody used to produce such humanized antibody. Preferably the humanized antibody will exhibit the same or substantially the same antigen-binding affinity and avidity as the parent antibody. Ideally, the affinity of the antibody will not be less than 10% of the parent antibody affinity, more preferably not less than about 30%, and most preferably the affinity will not be less than 50% of the parent antibody. Methods for assaying antigen-binding affinity are well known in the art and include half-maximal binding assays, competition assays, and Scat chard analysis. Suitable antigen binding assays are described in this application.

The present invention is directed to humanized monoclonal antibodies which bind human LT-β-R and their use as therapeutic agents. The present invention is further directed toward nucleic acid sequences which encode said humanized antibodies, and their expression in recombinant host cells. More specifically, the present invention is directed toward humanized antibodies derived from murine CBE11 which specifically binds to human LT-β-R.

Murine CBE11 (mCBE11) is a murine IgG1, kappa antibody isolated from a mouse immunized with a human LT-β-R-Ig fusion protein (Browning et al., *J. Immunol.* 154: 33 (1995)). mCBE11 functionally activates LT-β-R both in vitro and in vivo (PCT/US96/01386) and its isolation and anti-tumor properties have been described (Browning et al. *J. Exp. Med.* 183:867 (1996). The hybridism cell line which produces mCBE11 has been previously deposited with the American Type Culture Collection (ATCC) according to the provisions of the Budapest Treaty by the Applicants of the present invention and was assigned the ATCC accession number HB 11793. (PCT/US96/01386). Applicants have also shown that LT-β receptor cross-linking with various agonist anti-LT-β-R antibodies activate the LT-β receptor (i.e. can mimic the effects of the natural legends). (PCT/US96/01386) Receptor activation in turn has been shown to inhibit tumor growth in a variety of in vivo tumor models for which LT-β receptor is expressed. LT-β receptor has been shown to be expressed on a number of cancer cells including for example non small cell lung cancer cells (NSCLC), colorectal cancer cells (CRC), breast cancer cells, as well as on prostate, gastric, skin, stomach, esophagus and bladder cancer cells. Non-limiting examples of tumors that the agonist LT-β-R antibodies inhibit include the following solid tumors: HT29 colon Aden carcinoma, HT3 cervical carcinoma, A375 melanoma, MDA-231 breast carcinoma and primary colon tumors. Therefore, agonist LT-β-R antibodies possess properties which render it useful for treatment of diseases wherein LT-β-R activation and/or modulation of the LT-β-R/LT-β-R ligand interaction is desirable including for example the treating or reducing the advancement, severity or effects of neo-classic in a subject (e.g., human).

Humanizing the mCBE11 monoclonal antibody including the modeling analysis and back mutations required to substantially retain the binding properties of the mCBE11 monoclonal antibody is described herein.

Modeling Analysis of the Mouse Variable Regions

The CDRs contain the residues most likely to bind antigen and must be retained in the reshaped antibody. CDRs are defined by sequence according to Kabat et al., Sequence of Proteins of Immunological Interest, 5th Edition, The United States Department of Health and Human Services, The United States Government Printing Office, 1991. CDRs fall into canonical classes (Chothia et al, 1989 Nature, 342, 877-883) where key residues determine to a large extent the structural conformation of the CDR loop. These residues are almost always retained in the reshaped antibody. The polypeptide sequence of the light chain variable domain of mCBE11 is shown below with the CDR's underlined and the residue position numbers are designated according with the Kabat numbering system:

```
                                                    (SEQ ID NO:1)
  1  DIKMTQSPSS MYASLGERVT ITCKAGQDIK SYLSWYQQKP

41  WKSPKILIYY ATRLADGVPS RFSGSGSGQD YSLTISSLES

81  DDTATYYCLQ HGESPWTFGG GTKLEIK
```

The polypeptide sequence of the heavy chain variable domain of mCBE11 is shown below with the CDR's underlined and the residue position numbers are designated according with the Kabat numbering system:

```
                                                    (SEQ ID NO:2)
  1  EVQLVESGGG LVKPGGSLKL SCAASGFTFS DYYMYWFRQT

41  PEKRLEWVAT ISDGGSYTYY PDSVKGRFTI SRDNAKNNLY

81  LQMSSLKSED TAMYYCVREE NGNFYYEDYW GQGTTVTVSS
```

The variable light and heavy chains of mCBE11 were compared with the consensus sequences for mouse and human subgroups (Johnson, G., Wu, T. T. Kabat Database and its applications: future directions Nucleic Acid Research, 29, 205-206, 2001; Wu and Kabat, J. Exp. Med. 132:211-250 (1970)) using the program FASTA. The mCBE11 variable light chain is a member of mouse subgroup V with a 74% identity in 110 amino acid overlap and the mCBE11 variable heavy chain is a member of mouse subgroup IIId with a 79% identity in 132 amino acid overlap. The variable light chain corresponds to human subgroup I with a 66% identity in 113 amino acid overlap. The variable heavy chain corresponds to human subgroup III with a 71% identity in 131 amino acid overlap.

The CDRs of the present invention were classified into canonical classes. The L1 loop fell into canonical class 2 (11 residue loop), L2 into class 1 (7 residues) and L3 into class 1 (9 residues). The HI loop fell into class 1 (5 residues) and the H2 loop into class 3 (17) residues. The H3 loop did not belong to a canonical class.

The residues at the interface between the variable light and heavy chains have been defined (Chothia et al, 1985 J. Mol. Biol., 186, 651-663). These are usually retained in the reshaped antibody. In mCBE11 several of these residues are unusual at the interface, namely S34, I46, L89, H91 in VL and Y35, F37, V93, E95 in VH.

Unusual framework residues were determined by analyzing all mouse and human variable chain sequences in the September 1999 version of the Kabat database [NCBI, NIH]. It is believed that mCBE11-specific differences might indicate somatic mutations that enhance binding activity if these differences were close to the binding site. Unusual mouse residues further away from the binding site and unusual human residues were removed in case they would create immunogenic epitomes in the reshaped antibody. Unusual framework residues found in the mCBE11 were K3, M11, Y12, W41, Q69, S72, D81, T83 in the light chain; and F37, T40, E42, A49, N77 in the heavy chain. While most of these residues were not retained in the humanized CBE11 antibodies some of these unusual framework residues were retained including for example F37 and A49 in the heavy chains.

Modeling the Structure of the Variable Regions

The light and heavy chains of the present invention were aligned against the non-redundant database to determine structural frames to be used to construct three dimensional models of the mCBE11 light and heavy chains. Using BLAST the light chain was found to have 93% sequence identity to monoclonal murine antibody 5g9 (1AHW), and the heavy chain was found to have 81% sequence identity to murine IgG2A Fab fragment (Fab 17/9) (1 IFH). Using the molecular modeling package Sybyl (Tripos Inc.) the three dimensional structures of the light and heavy chains were built using the light chain of 5g9 and the heavy chain of IgG2A Fab fragment, respectively. The structural integrity of the models was assessed at the console and were found to be reasonable.

Design of the Reshaped Variable Regions

Homology matching was used to choose human acceptor frameworks to "accept" mCBE11 CDRs. Both the Kabat database and the non-redundant database from NCBI, ENTRZ (The National Institutes of Health) were searched using the software program BLAST. The choice of human acceptor frameworks was made based on sequence identity between mCBE11 frameworks and human frameworks (excluding frameworks from previously humanized antibodies).

The eventual choice of human frameworks was from antibody TNF-A1'CL (kabat ID 004770) against human tumor necrosis factor alpha (Griffiths et al, 1993 EMBO J. 12:725-734) for the variable light (VL) chain (human kappa subgroup I) and antibody FLA-IgG'CL (kabat id 040003) of unknown specificity (Malisan et al, 1996 Blood 87:717-724) for the variable heavy (VH) chain (human subgroup III). The human VL and VH frameworks have 15 and 11 residues differences compared to the murine sequences.

Back Mutations of the Human Frameworks

The most unpredictable procedure in the humanization of monoclonal antibodies is the identification of critical framework residues from the parent antibody (i.e. in the present case, the parent antibody is of mouse origin) that need to be retained in order to substantially retain the binding properties of the parent antibody while at the same time minimizing the potential immunogenicity of the resultant antibody. It is especially important to retain canonical residues, interface packing residues and unusual murine residues which are close to the binding site. In addition, residues in the 'Vernier Zone' (which forms a platform on which the CDRs rest) (Foote & Winter, 1992 J. Mol. Biol. 224, 487-499) and those close to CDR H3 are considered. Mutations back to the parent antibody (i.e. back mutating from human framework residues to mouse) are referred to herein as back mutations.

Three versions of the variable light reshaped chain (hu-CBE11 VL) and four versions of the variable heavy reshaped chain (hu-CBE11 VH) have been made. In general, the first version contains the most back mutations and the third version contains the fewest (ie the most "humanized") except for the fourth version of the hu-CBE11 VH. The present invention contemplates humanized antibodies derived from mCBE11 which possess a variable light chain selected from the variable light chains described below (i.e. VL#1, VL#2 or VL#3) and a variable heavy chain selected from the variable heavy chains described below (i.e. VH#1, VH#2, VHH2, or VH#4) in any combination.

(A) Light Chain:

3 Q (glutamine)≧K (lysine) It is retained in the first version since previous reshaping experiments have shown (e.g. Kolbinger et al, 1993 Prot. Eng., 6, 971-980) it might be important for antigen binding or CDR conformation.

41 G (lysine)≧W (tryptophan) It was retained in the first and second versions.

46 (leonine)≧I (isoleucine) It was retained in the first and second versions since it is both an interface residue and in the venire zone. In addition, it is an unusual reside occurring 9 times in mouse sequences and once in human. It is likely to affect the packing of the variable chains and may contact CDRs.

69 T (heroine)≧Q (glutamine) This residue is in the venire zone and may influence CDR conformation. The change from a short T to a longer Q may also mean that it contacts antigen. The Q is unusual occurring 58 times in mouse and twice in human. It was retained in the first version.

71 F (phenylalanine)≧Y (tyrosine) This residue is a canonical position and was retained in the all versions. It is also relatively unusual in human sequences only occurring 25 times.

(B) Heavy Chain

37 V (valise)≧F (phenylalanine) It was retained in the first, second and fourth versions.' The F at this position is unusual only occurring 15 times in mouse and 18 times in human. It is also an interface residue.

40 A (almandine)≧T (heroine) It was retained in the first version. Mutation at this position has been tried in 5 previous humanization experiments although never the change from A to T. One example is the change from A to S in the veneering of BrE-3 (Couto et al, 1994 Hybridism, 13, 215-219) in which binding affinity was increased, although the reason was never determined. In this case, the heavy chain was also human subgroup III.

49 S (serine)≧A (almandine) This residue is under the CDRs and in the venire zone and was retained in all versions.

89 V (valise)—>M (motioning) It was retained the first version. This position has been back-mutated in several humanization experiments. It was retained the first version.

93 A (almandine)≧V (valise) This position is both an interface residue and in the venire zone. It was retained in the first and second versions.

The amino acid and nucleic acid sequences of each of the different versions of the variable light and heavy chains made are as follows:

Reshaped Variable Light Chains

Reshaped variable light chain of CBE11—version 1 light chain (VL#1) (Plasmid pAND066)

```
  1  GATATTAAGATGACCCAGTCTCCATCATCCTTGTCTGCATCGGTGGGAGACAGGGTCACT   60
     D  I  K  M  T  Q  S  P  S  S  L  S  A  S  V  G  D  R  V  T
           aa3

61  ATCACTTGCAAGGCGGGTCAGGACATTAAAAGCTATTTAAGCTGGTACCAGCAGAAACCA  120
     I  T  C  K  A  G  Q  D  I  K  S  Y  L  S  W  Y  Q  Q  K  P

121  TGGAAAGCGCCTAAGATCCTGATCTATTATGCAACAAGGTTGGCAGATGGGGTCCCATCA  180
     W  K  A  P  K  I  L  I  Y  Y  A  T  R  L  A  D  G  V  P  S
        aa41           aa46

181  AGATTCAGTGGCAGTGGATCTGGGCAAGATTATACTCTAACCATCAGCAGCCTGCAGCCT  240
     R  F  S  G  S  G  S  G  Q  D  Y  T  L  T  I  S  S  L  Q  P
                          aa69 aa71

241  GAGGATTTCGCAACTTATTACTGTCTACAGCATGGTGAGAGCCCGTGGACGTTCGGTGGA  300
     E  D  F  A  T  Y  Y  C  L  Q  H  G  E  S  P  W  T  F  G  G

301  GGCACCAAGCTGGAGATCAAA                                         321
     G  T  K  L  E  I  K
                        40
```

SEQ ID NO: 3—represents the nucleic acid sequence of the reshaped VL#1 above.

SEQ ID NO: 4—represents the amino acid sequence of the reshaped VL#1 above.

Reshaped variable light chain of CBE11—version 2 light chain (VL#2) (Plasmid pAND070)

```
  1  GATATCCAGATGACCCAGTCTCCATCATCCTTGTCTGCATCGGTGGGAGACAGGGTCACT   60
     D  I  Q  M  T  Q  S  P  S  S  L  S  A  S  V  G  D  R  V  T

61  ATCACTTGCAAGGCGGGTCAGGACATTAAAAGCTATTTAAGCTGGTACCAGCAGAAACCA  120
     I  T  C  K  A  G  Q  D  I  K  S  Y  L  S  W  Y  Q  Q  K  P

121  TGGAAAGCGCCTAAGATCCTGATCTATTATGCAACAAGGTTGGCAGATGGGGTCCCATCA  180
     W  K  A  P  K  I  L  I  Y  Y  A  T  R  L  A  D  G  V  P  S
        aa41           aa46

181  AGATTCAGTGGCAGTGGATCTGGTACAGATTATACTCTAACCATCAGCAGCCTGCAGCCT  240
     R  F  S  G  S  G  S  G  T  D  Y  T  L  T  I  S  S  L  Q  P
                               aa71

241  GAGGATTTCGCAACTTATTACTGTCTACAGCATGGTGAGAGCCCGTGGACGTTCGGTGGA  300
     E  D  F  A  T  Y  Y  C  L  Q  H  G  E  S  P  W  T  F  G  G

301  GGCACCAAGCTGGAGATCAAA                                         321
     G  T  K  L  E  I  K
```

SEQ ID NO: 5—represents the nucleic acid sequence of the reshaped VL#2 above.
SEQ ID NO: 6—represents the amino acid sequence of the reshaped VL#2 above.

Reshaped variable light chain of CBE11—version 3 light chain (VL#3) (Plasmid pAND074)

```
  1  GATATCCAGATGACCCAGTCTCCATCATCCTTGTCTGCATCGGTGGGAGACAGGGTCACT   60
     D   I   Q   M   T   Q   S   P   S   S   L   S   A   S   V   G   D   R   V   T

61  ATCACTTGCAAGGCGGGTCAGGACATTAAAAGCTATTTAAGCTGGTACCAGCAGAAACCA  120
     I   T   C   K   A   G   Q   D   I   K   S   Y   L   S   W   Y   Q   Q   K   P

121  GGGAAAGCGCCTAAGCCTCTGATCTATTATGCAACAAGGTTGGCAGATGGGGTCCCATCA  180
     G   K   A   P   K   L   L   I   Y   Y   A   T   R   L   A   D   G   V   P   S

181  AGATTCAGTGGCAGTGGATCTGGTACAGATTATACTCTAACCATCAGCAGCCTGCAGCCT  240
     R   F   S   G   S   G   S   G   T   D   Y   T   L   T   I   S   S   L   Q   P
                                         aa71

241  GAGGATTTCGCAACTTATTACTGTCTACAGCATGGTGAGAGCCCGTGGACGTTCGGTGGA  300
     E   D   F   A   T   Y   Y   C   L   Q   H   G   E   S   P   W   T   F   G   G

301  GGCACCAAGCTGGAGATCAAA                                        321
     G   T   K   L   E   I   K
```

SEQ ID NO: 7—represents the nucleic acid sequence of the reshaped VL#3 above.
SEQ ID NO: 8—represents the amino acid sequence of the reshaped VL#3 above.

Reshaped Variable Heavy Chains:

Reshaped variable heavy chain of CBE 11—version 1 heavy chain (VH#1) (Plasmid pAND067)

```
  1  GAGGTACAACTGGTGGAGTCTGGGGGAGGCTTAGTGAAGCCTGGAGGGTCCCTGAGGCTC   60
     E   V   Q   L   V   E   S   G   G   G   L   V   K   P   G   G   S   L   R   L

61  TCCTGTGCAGCCTCTGGATTCACTTTCAGTGACTATTACATGTATTGGTTTCGCCAGACT  120
     S   C   A   A   S   G   F   T   F   S   D   Y   Y   M   Y   W   F   R   Q   T
                                                             aa37            aa40

121  CCGGGAAAGGGGCTGGAGTGGGTCGCAACCATTAGTGATGGTGGTAGTTACACCTACTAT  180
     P   G   K   G   L   E   W   V   A   T   I   S   D   G   G   S   Y   T   Y   Y
                                     aa49

181  CCAGACAGTGTGAAGGGGCGATTCACCATCTCCAGAGACAATGCCAAGAACAGCCTCTAC  240
     P   D   S   V   K   G   R   F   T   I   S   R   D   N   A   K   N   S   L   Y

241  CTGCAGATGAGCAGCCTGAGGGCTGAGGACACAGCCATGTATTACTGTGTAAGAGAGGAG  300
     L   Q   M   S   S   L   R   A   E   D   T   A   M   Y   Y   C   V   R   E   E
                                                 aa89            aa93

301  AATGGTAACTTTTACTACTTTGACTACTGGGGCCAAGGGACCACGGTCACCGTCTCCTCA  360
     N   G   N   F   Y   Y   F   D   Y   W   G   Q   G   T   T   V   T   V   S   S
```

SEQ ID NO: 9—represents the nucleic acid sequence of the reshaped VH#1 above.
SEQ ID NO: 10—represents the amino acid sequence of the reshaped VH#1 above.

Reshaped variable heavy chain of CBE11—version 2 heavy chain (VH#2) (Plasmid pAND071)

```
  1  GAGGTACAACTGGTGGAGTCTGGGGGAGGCTTAGTGAAGCCTGGAGGGTCCCTGAGGCTC   60
     E   V   Q   L   V   E   S   G   G   G   L   V   K   P   G   G   S   L   R   L

61  TCCTGTGCAGCCTCTGGATTCACTTTCAGTGACTATTACATGTATTGGTTTCGCCAGGCC  120
     S   C   A   A   S   G   F   T   F   S   D   Y   Y   M   Y   W   F   R   Q   A
                                                             aa37
```

```
121 CCGGGAAAGGGGCTGGAGTGGGTCGCAACCATTAGTGATGGTGGTAGTTACACCTACTAT   180
     P   G   K   G   L   E   W   V   A   T   I   S   D   G   G   S   Y   T   Y   Y
                                    aa49

181 CCAGACAGTGTGAAGGGGCGATTCACCATCTCCAGAGACAATGCCAAGAACAGCCTCTAC   240
     P   D   S   V   K   G   R   F   T   I   S   R   D   N   A   K   N   S   L   Y

241 CTGCAGATGAGCAGCCTGAGGGCTGAGGACACAGCTGTGTATTACTGTGTAAGAGAGGAG   300
     L   Q   M   S   S   L   R   A   E   D   T   A   V   Y   Y   C   V   R   E   E
                                                                    aa93

301 AATGGTAACTTTTACTACTTTGACTACTGGGGCCAAGGGACCACGGTCACCGTCTCCTCA   360
     N   G   N   F   Y   Y   F   D   Y   W   G   Q   G   T   T   V   T   V   S   S
```

SEQ ID NO: 11—represents the nucleic acid sequence of the reshaped VH#2 above.

SEQ ID NO: 12—represents the amino acid sequence of the reshaped VH#2 above.

Reshaped variable heavy chain of CBE11—version 3 heavy chain (VH#3) (Plasmid pAND075)

SEQ ID NO: 16—represents the amino acid sequence of the reshaped VH#4 above.

Antibodies consisting of different versions of the light and heavy chains were made and used for further studies. For instance, the antibody consisting of reshaped huCBE11 version 3 light variable chain (VL#3) and reshaped huCBE11

```
  1 GAGGTACAACTGGTGGAGTCTGGGGGAGGCTTAGTGAAGCCTGGAGGGTCCCTGAGGCTC    60
     E   V   Q   L   V   E   S   G   G   G   L   V   K   P   G   G   S   L   R   L

61 TCCTGTGCAGCCTCTGGATTCACTTTCAGTGACTATTACATGTATTGGGTGCGCCAGGCC   120
     S   C   A   A   S   G   F   T   F   S   D   Y   Y   M   Y   W   V   R   Q   A

121 CCGGGAAAGGGGCTGGAGTGGGTCGCAACCATTAGTGATGGTGGTAGTTACACCTACTAT   180
     P   G   K   G   L   E   W   V   A   T   I   S   D   G   G   S   Y   T   Y   Y
                                    aa49

181 CCAGACAGTGTGAAGGGGCGATTCACCATCTCCAGAGACAATGCCAAGAACAGCCTCTAC   240
     P   D   S   V   K   G   R   F   T   I   S   R   D   N   A   K   N   S   L   Y

241 CTGCAGATGAGCAGCCTGAGGGCTGAGGACACAGCTGTGTATTACTGCGCAAGAGAGGAG   300
     L   Q   M   S   S   L   R   A   E   D   T   A   V   Y   Y   C   A   R   E   E

301 AATGGTAACTTTTACTACTTTGACTACTGGGGCCAAGGGACCACGGTCACCGTCTCCTCA   360
     N   G   N   F   Y   Y   F   D   Y   W   G   Q   G   T   T   V   T   V   S   S
```

SEQ ID NO: 13—represents the nucleic acid sequence of the reshaped VH#3 above.

SEQ ID NO: 14—represents the amino acid sequence of the reshaped VH#3 above.

Reshaped variable heavy chain of CBE11—version 4 heavy chain (VH#4) (Plasmid pAND090)

version 4 heavy variable chain (VH#4), named huCBE11#4 or hCBE11, was made and cell lines, E46.4 and E77.4, producing the antibody were deposited with the A.T.C.C. depository (ATCC patent deposit designation PTA-3357 and 3765, respectively). The hybridoma cell lines E46.4 and E77.4 which produce huCBE11#4, or hCBE11, were deposited on

```
  1 GAGGTACAACTGGTGGAGTCTGGGGGAGGCTTAGTGAAGCCTGGAGGGTCCCTGAGGCTC    60
     E   V   Q   L   V   E   S   G   G   G   L   V   K   P   G   G   S   L   R   L

61 TCCTGTGCAGCCTCTGGATTCACTTTCAGTGACTATTACATGTATTGGTTTCGCCAGGCC   120
     S   C   A   A   S   G   F   T   F   S   D   Y   Y   M   Y   W   F   R   Q   A
                                                                    aa37

121 CCGGGAAAGGGGCTGGAGTGGGTCGCAACCATTAGTGATGGTGGTAGTTACACCTACTAT   180
     P   G   K   G   L   E   W   V   A   T   I   S   D   G   G   S   Y   T   Y   Y
                                    aa49

181 CCAGACAGTGTGAAGGGGCGATTCACCATCTCCAGAGACAATGCCAAGAACAGCCTCTAC   240
     P   D   S   V   K   G   R   F   T   I   S   R   D   N   A   K   N   S   L   Y

241 CTGCAGATGAGCAGCCTGAGGGCTGAGGACACAGCTGTGTATTACTGCGCAAGAGAGGAG   300
     L   Q   M   S   S   L   R   A   E   D   T   A   V   Y   Y   C   A   R   E   E

301 AATGGTAACTTTTACTACTTTGACTACTGGGGCCAAGGGACCACGGTCACCGTCTCCTCA   360
     N   G   N   F   Y   Y   F   D   Y   W   G   Q   G   T   T   V   T   V   S   S
```

SEQ ID NO: 15—represents the nucleic acid sequence of the reshaped VH#4 above.

May 4, 2001 and Oct. 5, 2001 with the American Type Culture Collection (ATCC) (10801 University Blvd (Manassas. Va.)

according to the provisions of the Budapest Treaty, and were assigned ATCC accession numbers PTA-3357 and PTA-3765, respectively. All restrictions on the availability to the public of the above ATCC deposits will be irrevocably removed upon the granting of a patent on this application.

The invention further contemplates equivalents and variants of the reshaped VH and VL sequences, i.e. those containing one or more conservative amino acid substitution which do not substantially affect LT-β-R binding. Humanized LT-β-R antibodies containing these humanized variable heavy and light sequences may be obtained by recombinant methods as described in the Examples.

Uses

The humanized anti-LT-β-R antibodies of the present invention have use in treating disease conditions wherein LT-β-R activation is therapeutically beneficial. Such conditions include treating, preventing or reducing the advancement, severity or effects of neoclassic.

In one embodiment of the invention is a method of treating a mammal (i.e. human) for a condition associated with undesired cell proliferation by administering to the mammal a therapeutically effective amount of a composition comprising humanized LT-β-R antibodies of the present invention.

In another embodiment of the invention is a method of treating a mammal (i.e. human) having a solid tumor (i.e. a carcinoma) that over expresses LT-β-R comprising administering to said mammal a humanized LT-β-R antibody that binds to LT-β-R in an amount effective to reduce the tumor volume. Examples of cancers whose cell proliferation is modulated by LT-β-R may be screened by measuring in vitro the level of LT-β-R and/or LT-β-R ligand (ie LTα1β2 or LIGHT) message expressed in tumor tissue libraries. Tumor tissue libraries in which of LT-β-R and/or LT-β-R ligand (ie LTα1β2 or LIGHT) message is highly expressed would be candidates. Tumor types contemplated in the present invention include solid tumors including but not limited to non small cell lung cancer (NSCLC), colorectal cancer (CRC), breast cancer, as well as on prostate, gastric, skin, stomach, esophagus and bladder cancer.

The humanized antibodies of the subject invention which are used in treating conditions associated with undesired cell proliferation, in particular tumor therapy, advantageously inhibit tumor cell growth, as measured for example by a decrease in the tumor volume, greater than about 10%, 20%, 30% or 40% and most advantageously greater than about 50%. The humanized antibodies are obtained through screening (see, for example, the discussion in Example 3). For example, humanized antibodies for use in the present invention can be selected on the basis of decreased tumor volume versus untreated cancer cells (e.g., greater than about 10%, 20%, 30%, 40% or 50%).

The present invention also provides pharmaceutical compositions comprising a humanized antibody of the present invention and a pharmaceutically acceptable recipient. Suitable carriers, for instance, and their formulations, are described in Remington' Pharmaceutical Sciences, 16$^{th}$ ed., 1980, Mack Publishing Co., edited by Oslo et al. Typically an appropriate amount of a pharmaceutically acceptable salt is used in the formulation to render the formulation isotonic. Examples of the carrier include buffers such as saline, Ringer's solution and dextrose solution. The pH of the solution is preferably from about 5 to about 8, and more preferably from about 7.4 to about 7.8. Further carriers include sustained release preparations such as semi permeable matrices of solid hydrophobic polymers, which matrices are in the form of shaped articles, e.g. liposome's, films or micro particles. It will be apparent to those of skill in the art that certain carriers may be more preferable depending upon for instance the route of administration and concentration of the pharmaceutical composition being administered.

Administration may be accomplished by injection (eg intravenous, intraperitoneal, subcutaneous, intramuscular) or by other methods such as infusion that ensure delivery to the bloodstream in an effective form.

The humanized antibodies of the present invention can be administered at an effective dose to treat the particular clinical condition addressed. Determination of a preferred pharmaceutical formulation and a therapeutically efficient dose regiment for a given application is well within the skill of the art taking. into consideration, for example, the weight and condition of the patient, the extent of the desired treatment and the tolerance of the patient for the treatment. For example, an effective dosage will be in the range of about 0.05 to about 100 milligrams per kilogram of body weight per day. More particularly, about 0.05 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 15 mg, 20 mg, or 25 mg, per kilogram body weight per day. Alternatively about 0.05 to about 100 milligrams, more particularly, about 0.05 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 15 mg, 20 mg, or 25 mg, per kilogram body weight per week. Alternatively about 0.05 to about 100 milligrams, more particularly, about 0.05 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 15 mg, 20, mg, or 25 mg, per kilogram body weight per two weeks. Alternatively about 0.05 to about 100 milligrams, more particularly, about 0.05 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 15 mg, 20 mg, or 25 mg, per kilogram body weight per three weeks. Alternatively about 0.05 to about 100 milligrams, more particularly, about 0.05 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 15 mg, 20 mg, or 25 mg, per kilogram body weight per four weeks.

Practice of the present invention will employ, unless indicated otherwise, conventional techniques of cell biology, cell culture, molecular biology, microbiology, recombinant DNA, protein chemistry, and immunology, which are within the skill of the art. Such techniques are described in the literature. See, for example, Molecular Cloning: A Laboratory Manual, 2nd edition. (Sam brook, Fritsch and Maneates, eds.), Cold Spring Harbor Laboratory Press, 1989; DNA Cloning, Volumes I and II (D. N. Glover, ed), 1985; Oligonucleotide Synthesis, (M. J. Gait, ed.), 1984; U.S. Pat. No. 4,683,195 (Mullis et al.,); Nucleic Acid Hybridization (B. D. Hames and S. J. Higgins, eds.), 1984; Transcription and Translation (B. D. Hames and S. J. Higgins, eds.), 1984; Culture of Animal Cells (R. I. Freshney, ed). Alan R. Liss, Inc., 1987; Immobilized Cells and Enzymes, IRL Press, 1986; A Practical Guide to Molecular Cloning (B. Perbal), 1984; Methods in Enzymology, Volumes 154 and 155 (Wu et al., eds), Academic Press, New York; Gene Transfer Vectors for Mammalian Cells (J. H. Miller and M. P. Calos, eds.), 1987, Cold Spring Harbor Laboratory; Immunochemical Methods in Cell and Molecular Biology (Mayer and Walker, eds.), Academic Press, London, 1987; Handbook of Experiment Immunology, Volumes I-IV (D. M. Weir and C. C. Blackwell, eds.), 1986; Manipulating the Mouse Embryo, Cold Spring Harbor Laboratory Press, 1986.

The following Examples are provided to illustrate the present invention, and should not be construed as limiting thereof.

EXAMPLES

Example 1

Construction and Expression of chCBE11 cDNAs encoding the murine CBE11 variable regions of the heavy and light chains were used to construct vectors for expression of murine-human chimeras (chCBE11) in which the muCBE11 variable regions were linked to human IgGI and kappa constant regions. For construction of the heavy chain chimera, a 0.36 kb PstI-BstEII fragment from the CBE11 heavy chain sub clone pEAG970 was sublimed into the phosphates 2.82 kb PstI-BstEII vector fragment from the 5a8 heavy chain plasmid pLCB7 (5a8 is a molecularly cloned CD4-specific mAb previously characterized at Biogen), to add a murine heavy chain signal sequence and splice donor site to the muCBE11 heavy chain variable region. In this plasmid, called pEAG979, the heavy chain mature N-terminus differs by two residues from the N-terminal sequence of purified authentic CBE11 heavy chain derived from Edman degradation, since it was primer-determined during PCR. To correct the heavy chain N-terminus, pEAG979 was subjected to unique site elimination (USE) mutagenesis using an Amersham Pharmacia Biotech USE mutagenesis kit following the manufacturer's recommended protocol. Mutated plasmids were identified by screening for introduced AvaII, PstI, and RsaI changes. The heavy chain sequence in the resultant plasmid pEAG981 was confirmed by DNA sequencing. The 0.44 kb NotI-HindIII heavy chain variable domain fragment from pEAG981 and the 1.21 kb HindIII-NotI fragment from the plasmid pEAG964, containing a human IgGI constant region, were sub cloned into the NotI site of the pCEP4 (Nitrogen) EBV expression vector-derived plasmid pCH269, producing plasmid pEAG983.

For construction of the light chain chimera, a 0.11 kb NotI-EcoRV fragment from the plasmid pMDR985 and a 0.37 kb EcoRV-BamHI fragment from the CBE 1 light chain variable domain plasmid pEAG967 were sub cloned into the phosphates 2.94 kb NotI-BamHII vector fragment from Stratagene's pBluescriptIISK+cloning vector, to add a murine light chain signal sequence and a 5' NotI site in the resulting plasmid pEAG978. This plasmid was subjected to USE mutagenesis using an Amersham Pharmacia Biotech USE mutagenesis kit following the manufacturer's recommended protocol, with mutagenic primers which encoded a V3K substitution to match the authentic CBE11 light chain N-terminus, and which introduced a BglII site at the 3' end of the light chain variable domain. Mutated plasmids were identified by screening for introduced BgII, EcoRV, and MseI site changes. The light chain sequence in the resultant plasmid pEAG980 was confirmed by DNA sequencing. The 0.41 kb NotI-BgIII light chain variable domain fragment from pEAG980 and the 0.68 kb BcII-NotI fragment from the plasmid pEAG963, containing a human kappa light chain constant domain, were sub cloned into the NotI site of the pCEP4 (Nitrogen) EBV expression vector-derived plasmid pCH269, producing plasmid pEAG982.

Expression vectors (chCBE11 heavy chain vector pEAG983 and chCBE11 light chain vector pEAG982) were co-transfected into 293-EBNA cells and transected cells were tested for antibody secretion and specificity (empty vector- and ch5c8 (a molecularly cloned CD 154-specific mAb previously characterized at Biogen)-transected cells served as controls). Western blot analysis (developed with anti-human heavy and light chain antibodies) of protein A immunoprecipitates from whole cell lysates and conditioned medium indicated that chCBE11-transected cells synthesized and efficiently secreted heavy and light chains at levels similar to ch5c8-transected cells. FACS analysis of LT-β-R -expressing HT-29 cells stained with conditioned medium from transected cells indicated that the chCBE11 antibody bound and produced staining patterns similar to those of muCBE11, while conditioned medium from mock- and ch5c8-transected cells failed to stain LT-β-R on HT-29 cells. Chimerical CBE11 produced from transient transfect ion was purified and demonstrated to induce IL-8 secretion by LT-β-R -expressing A375 melanoma cells and to inhibit growth of Wider Aden carcinoma cells in nude mice.

Example 2

Construction and Expression of huCBE11

Design of the reshaped variable domains to produce humanized CBE11 (huCBE11) was carried out as described supra. The choice of the human acceptor frameworks was by homology matching: human kappa subgroup I mAb TNF-A1 for the light chain (Griffiths et al., 1993), and human subgroup III mAb FLA-IgG for the heavy chain (Malisan et al., 1996). Three versions of each of the variable light and four versions of the variable heavy reshaped chains were designed. In general the first version contains the most back mutations to the murine donor sequences, while the last version contains the fewest (i.e., the most "humanized").

The huCBE11 variable regions were made by unique site elimination (USE) mutagenesis using an Amersham Pharmacia Biotech USE mutagenesis kit following the manufacturer's recommended protocol, using the chCBE11 variable domain plasmids as starting templates. The mutagenic primers for the framework (FR) changes are described below. The cDNA sequence of the human acceptor frameworks (Kabat database #004770 for the light chain and Kabat #040003 for the heavy chain) were used, with silent mutations introduced to produce restriction site changes to facilitate identification of mutated plasmids. Mutated plasmids were identified by identified by screening for the introduced restriction site changes. The variable region cDNA sequences in the resultant plasmids were confirmed by DNA sequencing.

VH#1 used pEAG981 template with the following primers: FR1 primer 5' GCC TGG AGG GTC CCT GAG GCT CTC CTG TGC AGC CTC 3' (SEQ ID NO:17), which introduced a Bsu36I site; FR2 primer 5' GTT TCG CCA GAC TCC GGG AAA GGG GCT GGA GTG GGT CGC AAC 3' (SEQ ID NO:18), which introduced NciI and HpaII sites; and FR3 primer 5' CAG AGA CAA TGC CAA GAA CAG CCT CTA CCT GCA GAT GAG CAG CCT GAG GGC TGA GGA CAC AGC CAT G 3' (SEQ ID NO:19), which introduced Bsu36I and PstI sites and removes an RsaI site. The resultant VH#I plasmid was designated pAND067.

VH#2 used pAND067 template with the following primers: FR2 primer 5' CAT GTA TTG GTT TCG CCA GGC CCC GGG AAA GGG GCT GG 3' (SEQ ID NO:20), which introduced a SmaI site; and FR3 primer 5' GGG CTG AGG ACA CAG CTG TGT ATT ACT GTG TAA GAG 3' (SEQ ID NO:21), which introduced a PvuII site. The resultant VH#2 plasmid was designated pAND071.

VH#3 used plasmid pAND067 template with the following primers: FR2 primer 5' GTG ACT ATT ACA TGT ATT GGG TGC GCC AGG CCC CGG GAA AGG GGC TGG AG 3'

(SEQ ID NO:22), which introduced SmaI and HhaI sites; and FR3 primer 5' GAG GGC TGA GGA CAC AGC TGT GTA TTA CTG CGC AAG AGA GGA GAA TGG TAA C 3' (SEQ ID NO:23), which introduced PvuII and FspI sites. The resultant VH#3 plasmid was designated pAND075.

Expression vectors for the huCBE11 heavy chains were made by sub cloning the 0.44 kb NotI-HindIII heavy chain variable domain fragments from pAND067, pAND071, or pAND075, and the 1.21 kb HindII-NotI fragment from the plasmid pEAG964, containing a human IgGI constant region, were sub cloned into the NotI site of the pCEP4 EBV expression vector-derived plasmid pCH269, producing heavy chain expression vectors pAND069 (VH#1), pAND073 (VH#2), and pAND077 (VH#3).

VL#1 used plasmid pEAG980 template with the following primers: FR1 primer 5' CTT GCA AGT GAT AGT GAC CCT GTC TCC CAC CGA TGC AGA CAA GGA TGA TGG AGA CTG GGT CAT C 3' (SEQ ID NO:24), which removed HinfI and NsiI sites; FR2 primer 5' CAT AAT AGA TCA GGA TCT TAG GCG CTT TCC ATG GTT TCT GCT G 3' (SEQ ID NO:25), which introduced HaeI and HhaI sites; and FR3 primer 5' GTA GAC AGT AAT AAG TTG CGA AAT CCT CAG GCT GCA GGC TGC TGA TGG TTA GAG TAT AAT CTT GCC CAG ATC 3' (SEQ ID NO:26), which introduced Bsu36I, DdeI, and PstI sites. The resultant VL#1 plasmid was designated pAND066.

VL#2 used plasmid pAND066 template with the following primers: FR1 primer 5' GAT GGA GAC TGG GTC ATC TGG ATA TCA CCT CTG GCA CCT G 3' (SEQ ID NO:27), which introduced an EcoRV site; and FR3 primer 5' GAT GGT TAG AGT ATA ATC TGT ACC AGA TCC ACT GCC ACT G 3' (SEQ ID NO:28), which introduced an RsaI site. The resultant VL#2 plasmid was designated pAND070.

VL#3 used plasmid pAND066 template with the following primers: FR1 primer 5' GAT GGA GAC TGG GTC ATC TGG ATA TCA CCT CTG GCA CCT G 3' (SEQ ID NO:29), which introduced an EcoRV site; FR2 primer 5' CAA CCT TGT TGC ATA GAT CAG AAG CTT AGG CGC TTT CCC TGG TTT CTG GTA CC 3' (SEQ ID NO:30), which introduced a HindIII site and removed NCOs and StyI sites; and FR3 primer 5' GAT GGT TAG AGT ATA ATC TGT ACC AGA TCC ACT GCC ACT G 3' (SEQ ID NO:31), which introduced an RsaI site. The resultant VL#3 plasmid was designated pAND074.

Expression vectors for the huCBE11 light chains were made by sub cloning the 0.41 kb NotI-BglII light chain variable domain fragments from pAND066, pAND070, or pAND074 and the 0.68 kb BclI-NotI fragment from the plasmid pEAG963, containing a human kappa light chain constant domain, were sub cloned into the NotI site of the pCEP4 EBV expression vector-derived plasmid pCH269, producing light chain expression vectors pAND068 (VL#1), pAND072 (VL#2), and pAND076 (VL#3).

Expression vectors were co-transfected into 293-EBNA cells and transfected cells were tested for antibody secretion and specificity (empty vector-transfected cells served as negative control). Western blot analysis (developed with anti-human heavy and light chain antibodies) of protein A immunoprecipitates from whole cell lysates and conditioned medium indicated that huCBE11-transfected cells synthesized and efficiently secreted heavy and light chains at levels similar to chCBE11-transfected cells. FACS analysis of LT-β-R -expressing HT-29 cells stained with conditioned medium from transfected cells indicated that the huCBE11 #3 mAb bound less well than huCBE11 #1 and huCBE11 #2 mAbs relative to chCBE11 (Table 1 below) where huCBE11 #1 (VL#1 with VH#1); huCBE# 2 (VL#2 with VH#2) and huCBE11 #3 (VL#3 with VH#3). Mix and match co-transfect ions suggested that the reduction could be attributed to the VH#3, which differed from VH#2 at two framework residues: FR2 F37V and FR3 V93A. To examine the individual contributions of each of these changes, new heavy chain expression vectors were constructed. Plasmid pAND089, the F37V variant of VH#2, was made by sub cloning the 311 bp NotI-PstI fragment from pAND075, the 126 bp PstI-HindIII fragment from pAND071, and the 1.21 kb HindIII-NotI fragment from the plasmid pEAG964 into the NotI site of the pCEP4 EBV expression vector-derived plasmid pCH269. Plasmid pAND090, the V93A variant of VH#2, was made by sub cloning the 311 bp NotI-PstI fragment from pAND071, the 126 bp PstI-HindIII fragment from pAND075, and the 1.21 kb HindIII-NotI fragment from the plasmid pEAG964 into the NotI site of the pCEP4 EBV expression vector-derived plasmid pCH269. These H2/H3 chimerical heavy chains were co-transfected into 293-EBNA cells with VL#2 or VL#3. FACS analysis indicated that the V93A H2 variant restored LT-β-R binding when paired with the VL#3 (Table 1 supra). The pAND076 and pAND090 pairing was designated huCBE11 #4 (Table 1 supra).

Co-transfect ions of 293-EBNA cells with chCBE11 and huCBE11 versions #1-4 were scaled up and conditioned medium was harvested. Antibody was purified on Protein A-Sparse. Purified mAbs were assayed for activity.

TABLE 1

FACS staining of HT-29 cells by chCBE11 and huCBE11

| | Light chain | Heavy chain | Relative MFI |
|---|---|---|---|
| ChCBE11 | pEAG982 | pEAG983 | 1.00 |
| HuCBE11#1 | pAND068 | pAND069 | 1.00 |
| HuCBE11#2 | pAND072 | pAND073 | 1.00 |
| HuCBE11#3 | pAND076 | pAND077 | 0.62 |
| L2/H3 | pAND072 | pAND077 | 0.42 |
| L3/H2 | pAND076 | pAND073 | 1.00 |
| L2/F37V H2 | pAND072 | pAND089 | 0.65 |
| L2/V93A H2 | pAND072 | pAND090 | 0.75 |
| L3/F37V H2 | pAND076 | pAND089 | 0.80 |
| HuCBE11#4 | pAND076 | pAND090 | 1.00 |

Conditioned medium from transiently transfected cells was used to stain HT-29 cells by incubating for 30 min on ice, washing cells twice with FACS buffer (PBS with 5% FBS and 0.05% sodium aside), staining with PE-conjugated anti-human IgG (H+L), Jackson ImmunoResearch Laboratories, Inc., for 30 min on ice in FACS buffer, washing cells twice with FACS buffer, and resuspending in FACS buffer for analysis.

Relative MFI refers to mean MFI normalized to that observed for chCBE11. Data shown represents the average from two independent transfect ions.

Example 3

IL-8.Agonist on A375 Cells

Figure 1B:
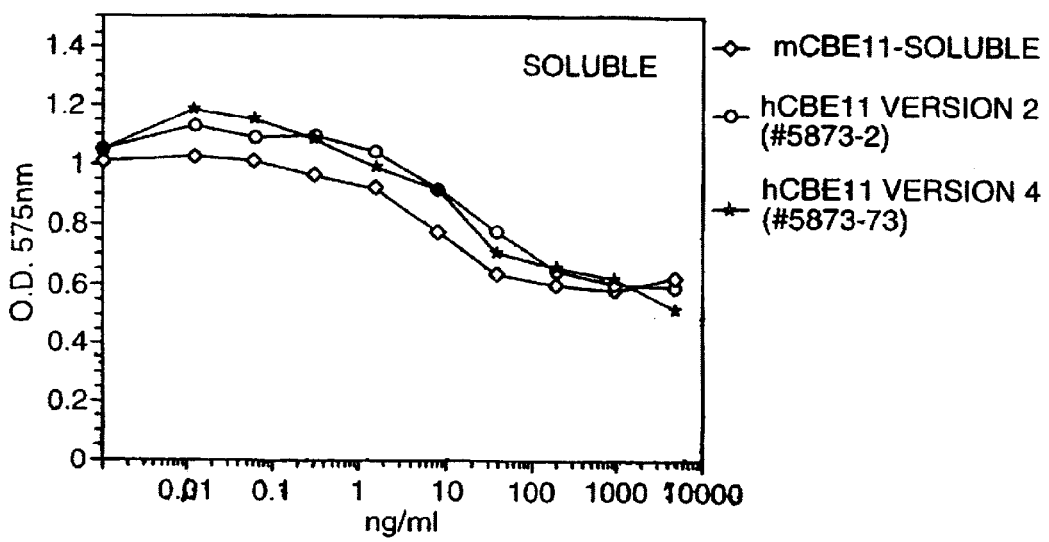

Purified mAbs were assayed for activity. Results of an IL-8 release assay on A375 human melanoma cells are shown in FIGS. 1A and 1B which measure the amount of IL-8 released upon the binding of anti-LT-β-R antibodies with an LT-β-R expressed on the surface of A375 human melanoma cells. A375 cells were plated at 10⁵/ml into 96 well plates containing either soluble antibodies or antibodies captured onto goat anti-human IgG Fc (Jackson ImmunoResearch Laboratories)-coated wells. The culture plates were incubated overnight. Conditioned medium was harvested and analyzed for IL-8 by ELISA.

Example 4

Cytotoxicity on Wider Cells

Figure 2B:
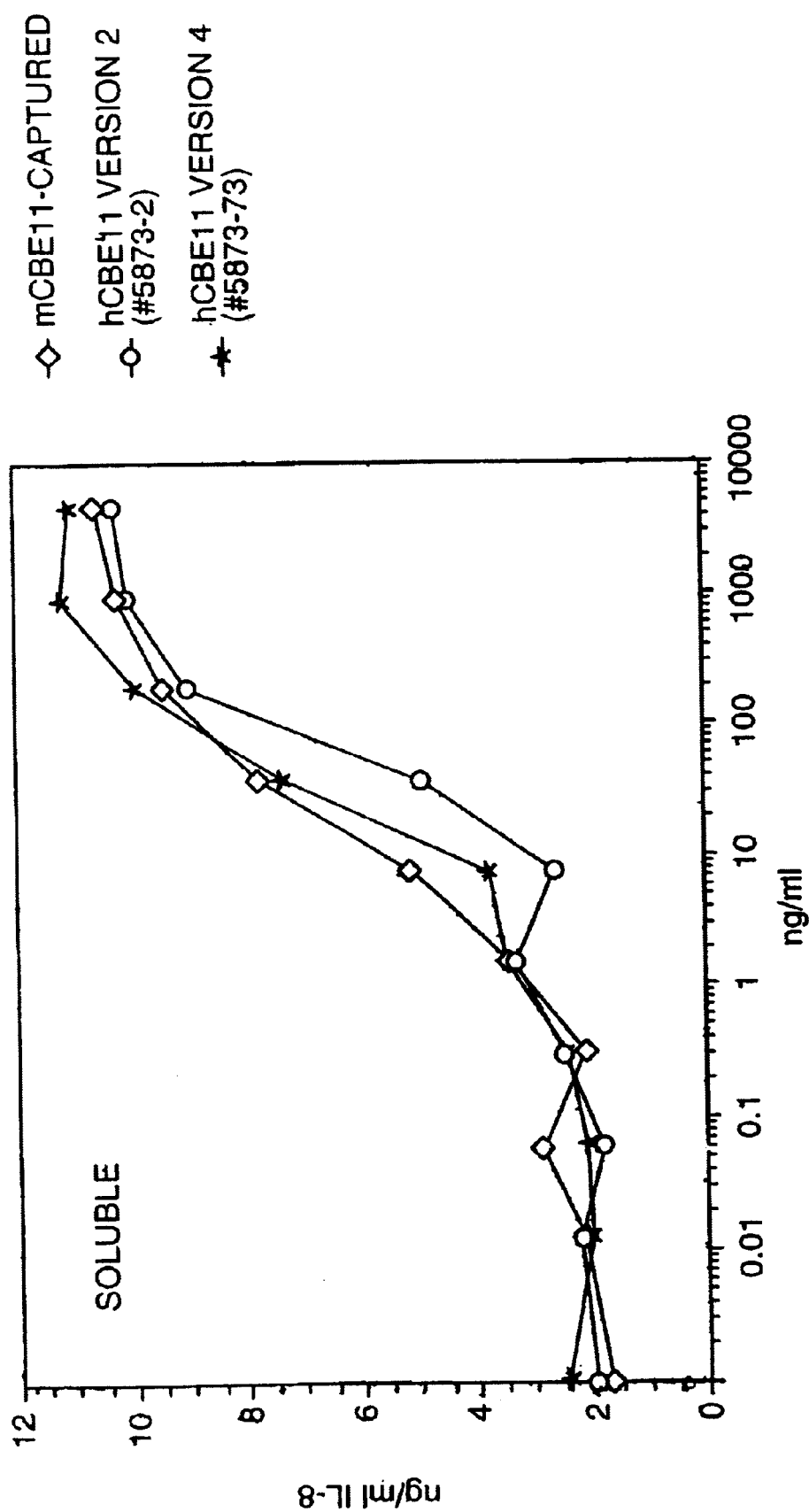

Results of a cytotoxicity assay using WiDr colon cancer cells with soluble anti-LT-β-R antibodies onto anti-human IgG Fc coated wells which demonstrate that anti-LT-β-R antibodies increases cytotoxicity in cancer cells as shown in FIGS. 2A and 2B. WiDr cells were plated at $6 \times 10^4$/ml in the presence of 80 units/ml huIFN-gamma into 96 well plates containing either soluble antibodies or antibodies captured onto goat anti-human IgG Fc (Jackson ImmunoResearch Laboratories)-coated wells. The culture plates were incubated for 5 days. MTT was added for 4 hrs and the resulting precipitate was dissolved by overnight incubation with 10% SDS in 10 mM HCl, and O.D.s were read on a microplate reader.

Example 5

The antibody consisting of reshaped huCBE11 version 3 light variable chain (VL#3) and reshaped huCBE11 version 4 heavy variable chain, named huCBE11 #4 or hCBE11, was made and the cell line producing the antibody was deposited with the A.T.C.C. depository (ATCC patent deposit designation PTA-3357). The full polypeptide sequences of each of the light and heavy chains, including the constant domains are as follows:

Sequence of mature huCBE11 version 3 light chain (SEQ ID NO:32):

```
  1 DIQMTQSPSS LSASVGDRVT ITCKAGQDIK SYLSWYQQKP GKAPKLLIYY
 51 ATRLADGVPS RFSGSGSGTD YTLTISSLQP EDFATYYCLQ HGESPWTFGG
101 GTKLEIK|RTV AAPSVFIFPP SDEQLKSGTA SVVCLLNNFY PREAKVQWKV
151 DNALQSGNSQ ESVTEQDSKD STYSLSSTLT LSKADYEKHK VYACEVTHQG
201 LSSPVTKSFN RGEC|
```

CDRs are underlined; back mutation F71Y is bolded; constant domain is bracketed.

Sequence of mature huCBE11 version 4 heavy chain (SEQ ID NO:33):

```
                                       V37F        S49A
  1 EVQLVESGGG LVKPGGSLRL SCAASGFTFS DYYMYWFRQA PGKGLEWVAT
 51 ISDGGSYTYY PDSVKGRFTI SRDNAKNSLY LQMSSLRAED TAVYYCAREE
101 NGNFYYFDYW GQGTTVTVSS |ASTKGPSVFP LAPSSKSTSG GTAALGCLVK
151 DYFPEPVTVS WNSGALTSGV HTFPAVLQSS GLYSLSSVVT VPSSSLGTQT
201 YICNVNHKPS NTKVDKKVEP KSCDKTHTCP PCPAPELLGG PSVFLFPPKP
251 KDTLMISRTP EVTCVVVDVS HEDPEVKFNW YVDGVEVHNA KTKPREEQYN
301 STYRVVSVLT VLHQDWLNGK EYKCKVSNKA LPAPIEKTIS KAKGQPREPQ
351 VYTLPPSRDE LTKNQVSLTC LVKGFYPSDI AVEWESNGQP ENNYKTTPPV
401 LDSDGSFFLY SKLTVDKSRW QQGNVFSCSV MHEALHNHYT QKSLSLSPG|
```

CDRs are underlined; back mutations V37F and S49A are bolded; constant domain is bracketed.

Figure 3:
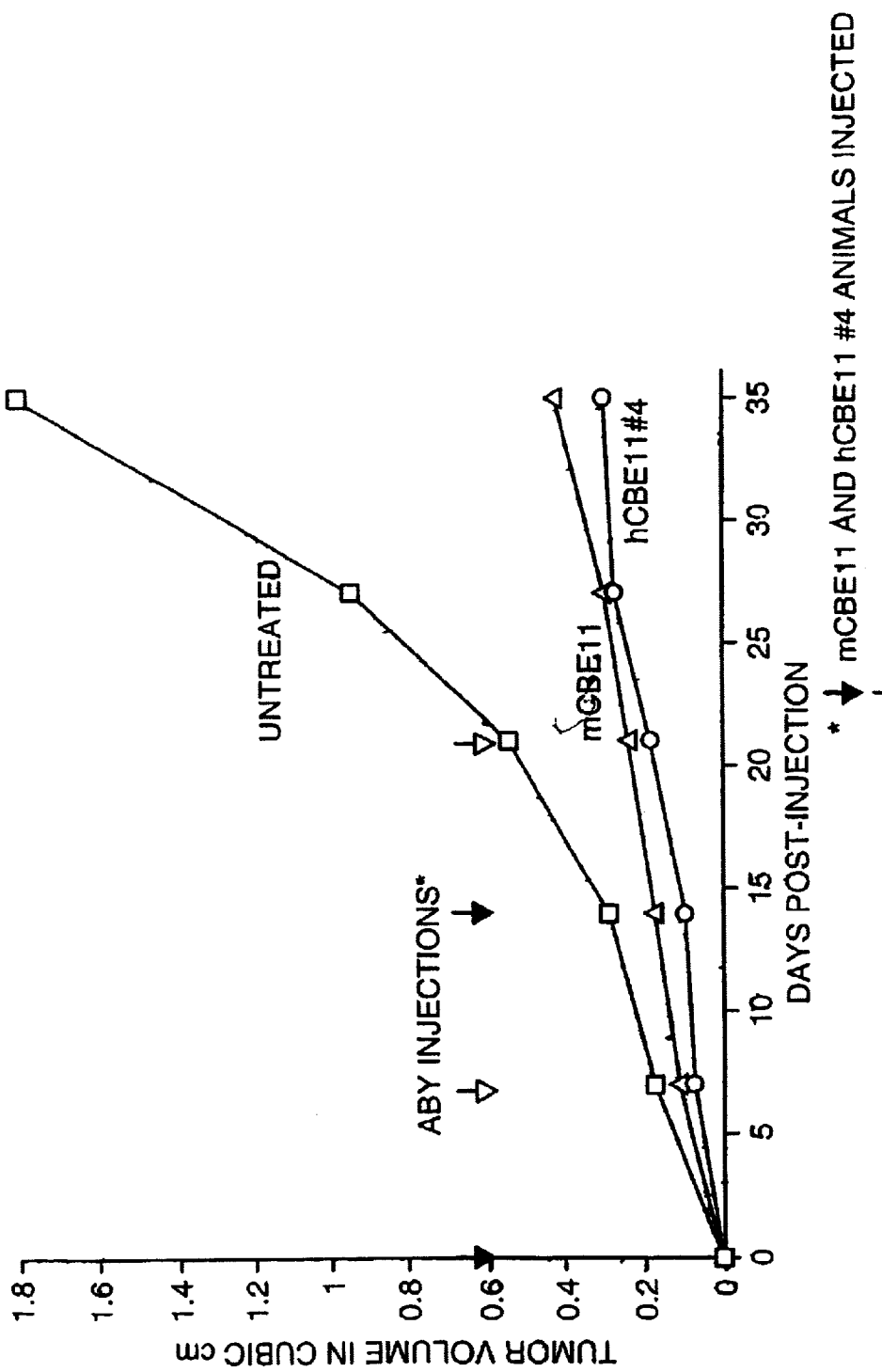
FIG. 3 shows a graph of tumor volume versus days of administration. mCBE11 (triangles), hu CBE11 #4 (humanized anti-LT-β-R antibody comprising version 3 of the light chain (VL#3) and version 4 of the heavy chain (VH#4)) (circles), no treatment (squares).
Figure 4:
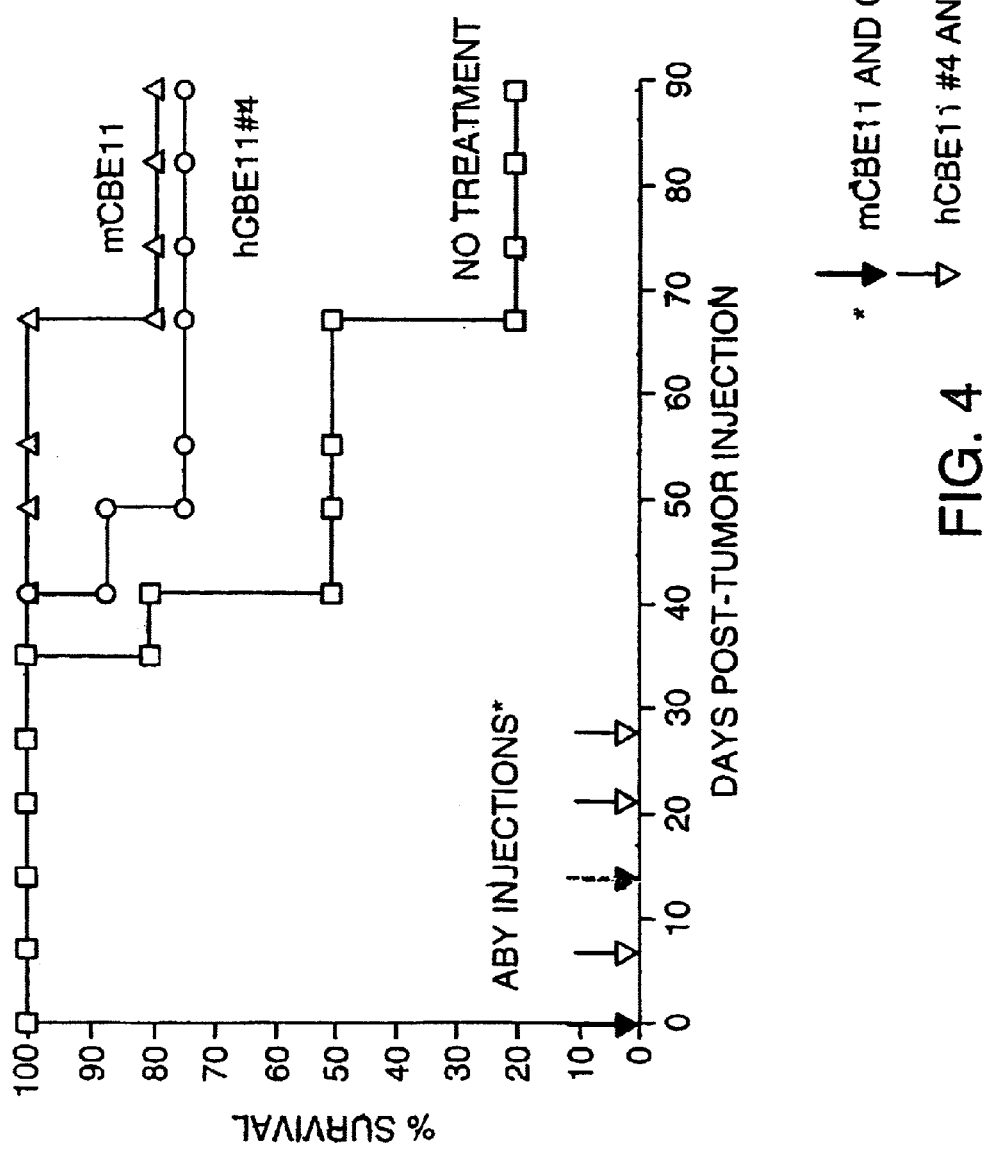
FIG. 4 shows a graph of percent survival of animals versus days of post tumor injection. mCBE11 (triangles), huCBE11 #4 (humanized anti-LT-β-R antibody comprising version 3 of the light chain and version 4 of the heavy chain) (circles), no treatment (squares).

6 week old nude mice were injected intraperitoneally with 100 ug of anti-LFA3 antibody (1E6), 100 ug anti-LTβR antibody (huCBE11 #4) or not injected (control). The animals were then injected subcutaneously with $1 \times 10^6$ WIDR colon Aden carcinoma cells. The huCBE11 #4-treated mice were retreated weekly with 100 ug of antibody and the mCBE11 animals were retreated on day 14 only. Tumor size was measured weekly and the volume of the tumor sphere calculated (FIG. 3). Animals were sacrificed when their tumors reached a volume of 2.0 cm³ (16 mm diameter) and their death was noted on the survival chart (FIG. 4).

Example 6

Figure 5:
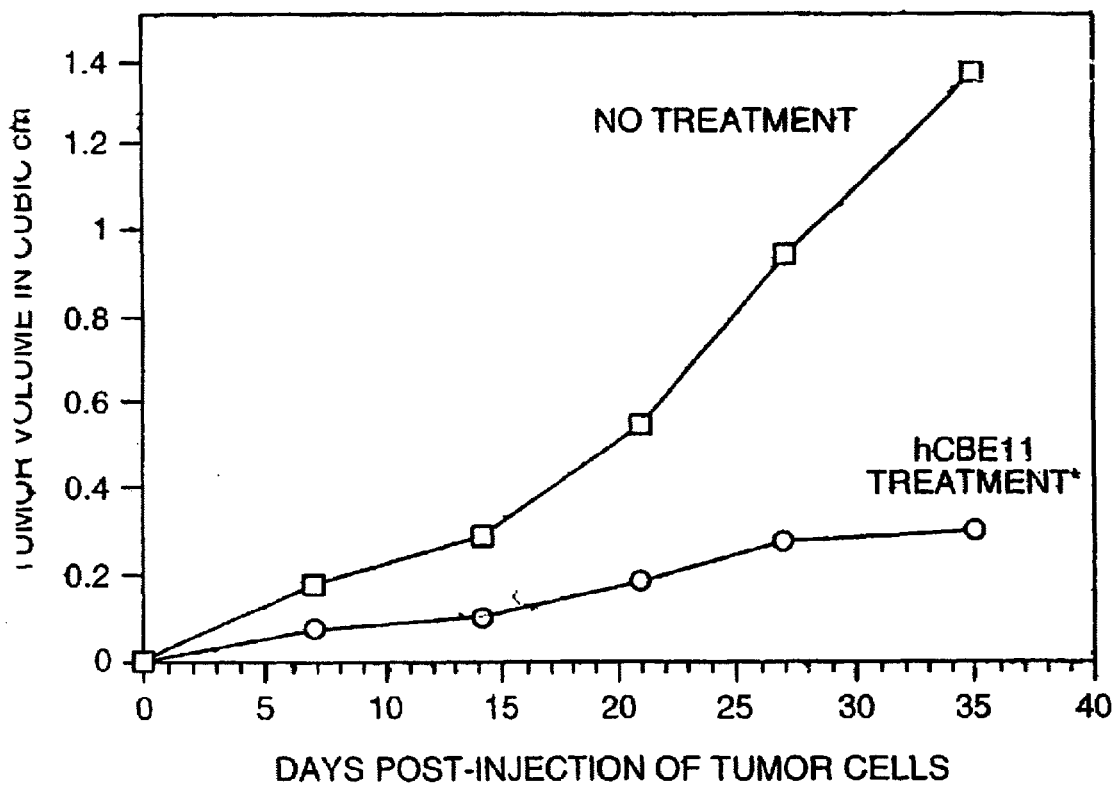
FIG. 5 shows a graph of tumor volume versus days post-injection. HuCBE11 #4 (humanized anti-LT-β-R antibody comprising version 3 of the light chain (VL#3) and version 4 of the heavy chain (VH#4)) (circles) and control with no treatment (squares).

6 week old nude mice were either injected intraperitoneally with 100 ug anti-LTβR antibody (huCBE11 #4) or were not injected (control). All animals were then injected subcutaneously with 1×10⁶ WIDR colon adenocarcinama cells. The huCBE11 #4-treated mice were retreated weekly with 100 ug of huCBE11 #4. Tumor size was measured weekly and the volume of the tumor sphere calculated. Tumor volumes shown represent the average of 10 control animals and 8 huCBE11 #4-treated animals (FIG. 5).

Weekly treatment with huCBE11 #4 significantly inhibits the growth rate of WIDR tumors implanted subcutaneously in nude mice. Animals treated with antibody through day 21 continue to show reduced tumor growth rates two week following the cessation of treatment.

Figure 6:
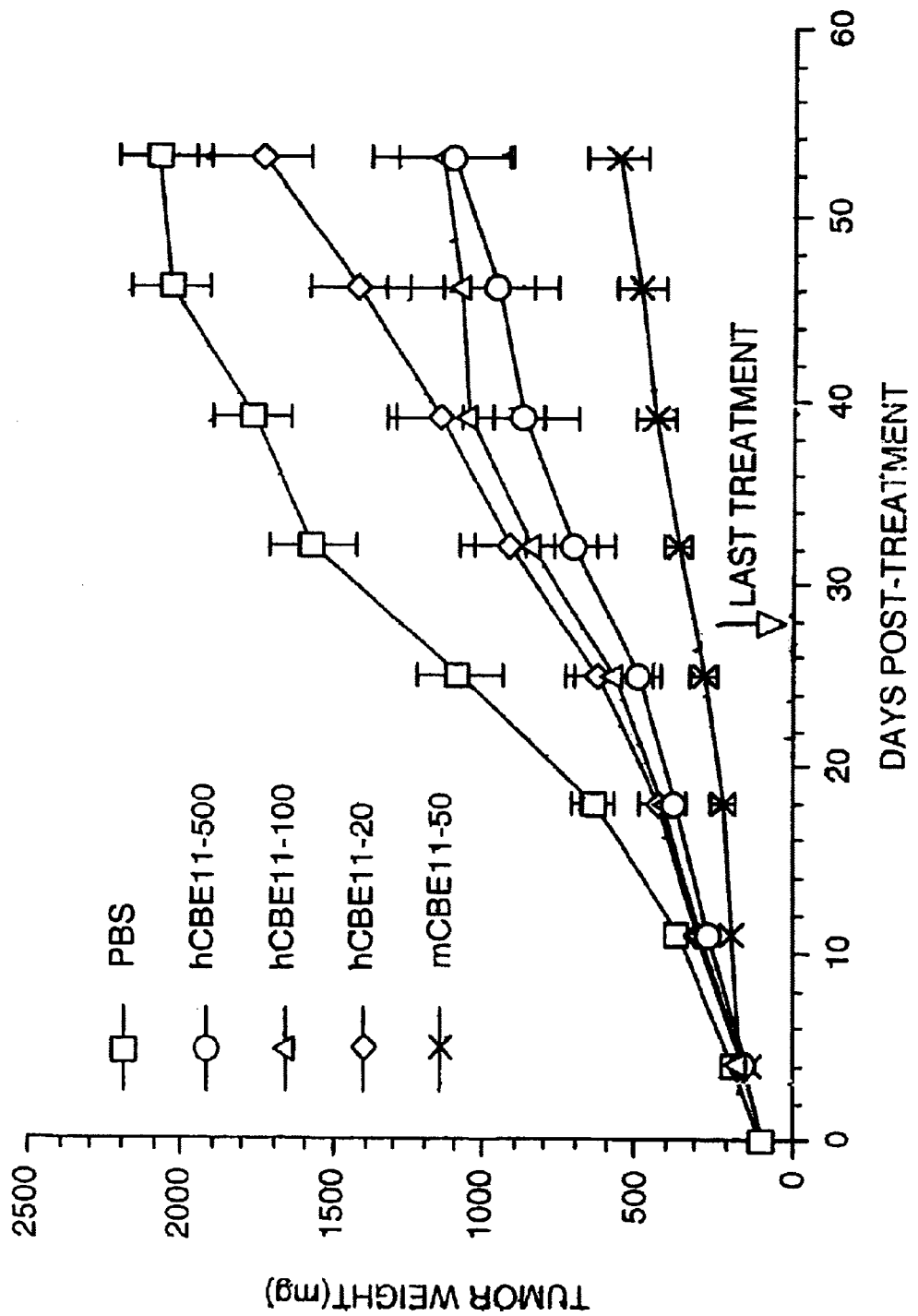
FIG. 6 shows a graph of pre-grown tumor volume versus days of post-treatment. Control (square); huCBE11 #4 (humanized anti-LT-β-R antibody comprising version 3 of the light chain (VL#3) and version 4 of the heavy chain (VH#4)) at different dosages:500 ug (circles), 100 ug (triangles), and 20 ug (diamonds); mCBE11 (crosses).

Example 7 huCBE11 #4 Slows Growth of Pregrown WIDR Tumors and Increases Survival in WIDR Tumor-bearing Nude Mice $10^6$ WIDR cells were reground subcutaneously for 10 days in Nude mice. The mice received subcutaneous injections of either PBS or huCBE11 #4 weekly or mCBE11 alternate weeks. Tumor weights were calculated from width and length measurements and animals with tumors over 2000 mg were sacrificed, their tumor weights at time of sacrifice continued into the statistical averaging. Error bars represent standard error. Tumor weights were calculated using the formula: (Width×Length)/2=tumor weight in mg. The results are graphed in FIG. 6 and show that huCBE11 #4 is able to slow pre-grown tumors in vivo.

Figure 7:
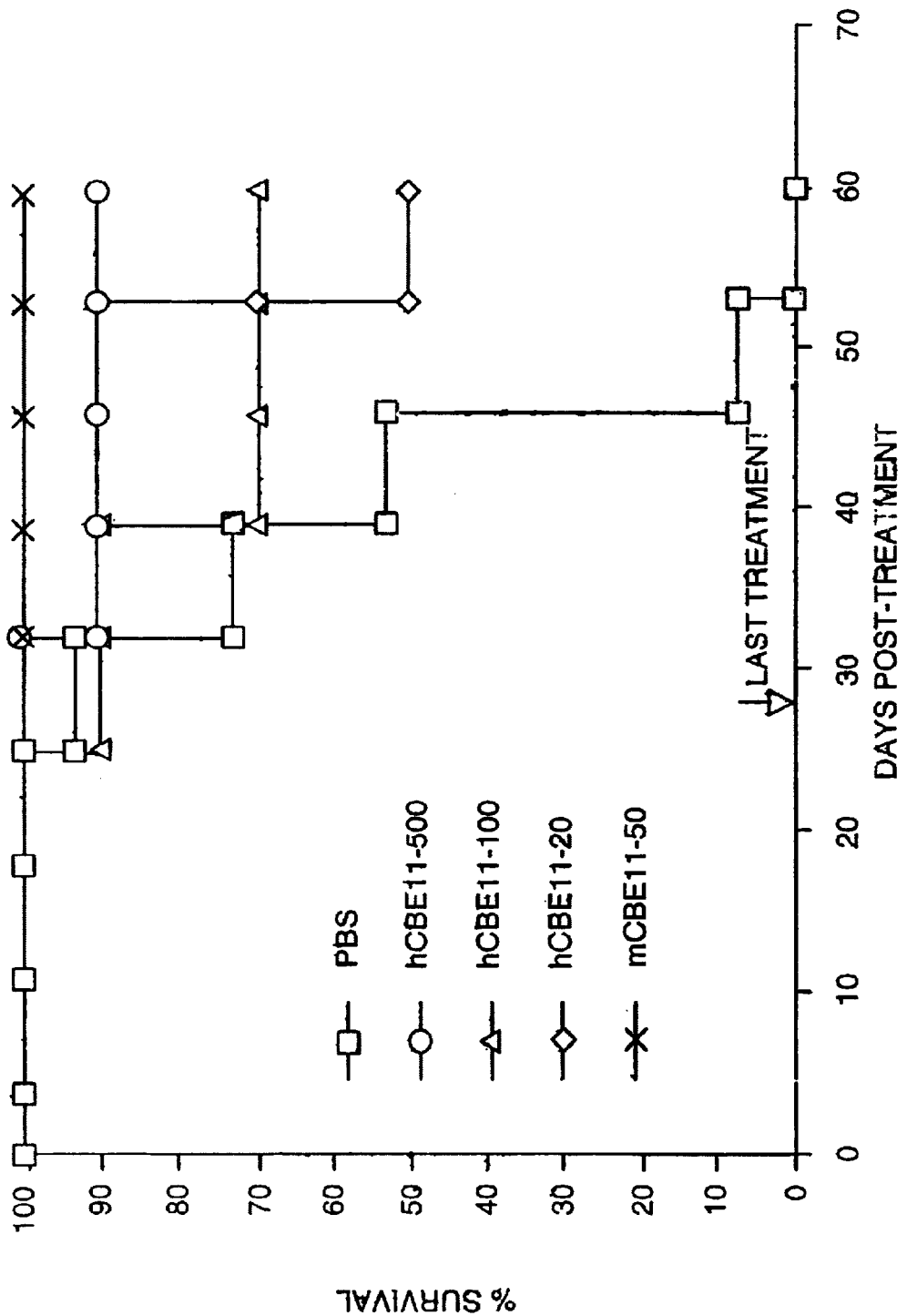
FIG. 7 shows a graph of percent survival of animals with pre-grown tumors versus days of post-treatment. Control (square); huCBE11 #4 (humanized anti-LT-β-R antibody comprising version 3 of the light chain (VL#3) and version 4 of the heavy chain (VH#4)) at different dosages:500 ug (circles), 100 ug (triangles), and 20 ug (diamonds); mCBE11 (crosses).
Figure 8:
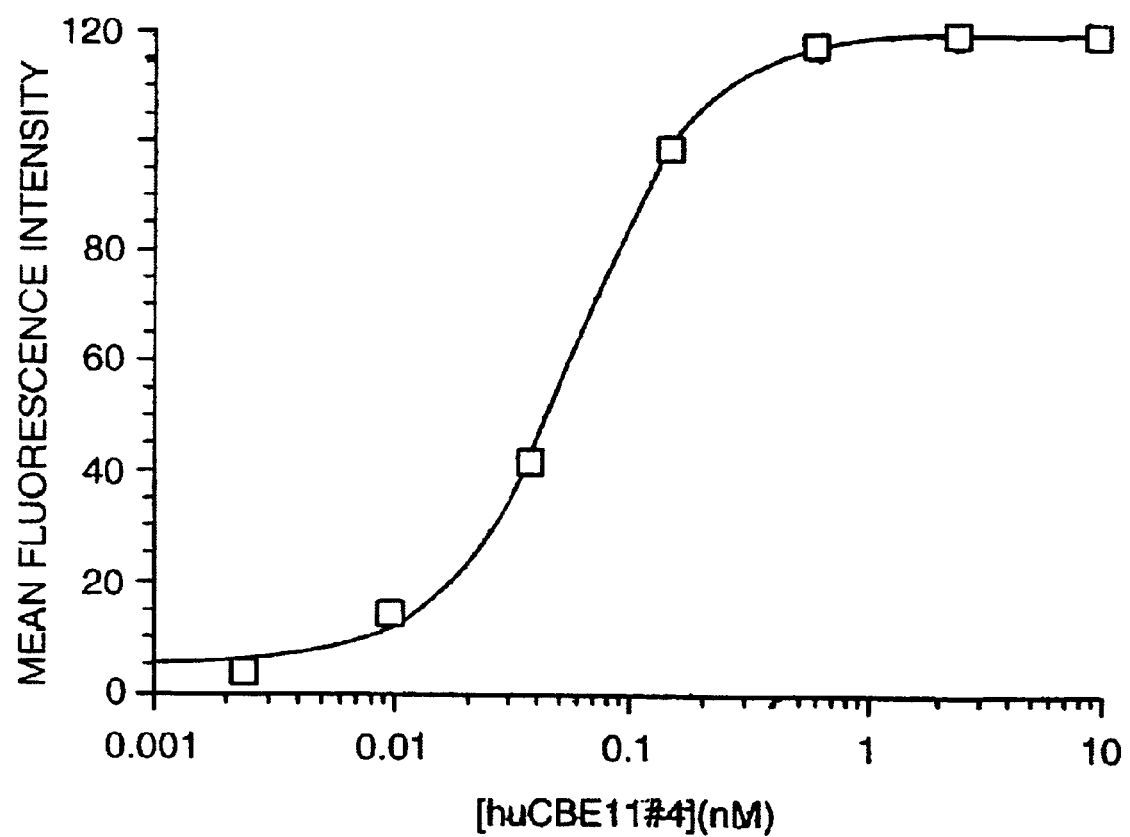
FIG. 8 shows a graph of mean fluorescence intensity versus huCBE11 #4 concentrations on a log scale.

In addition, tumors were grown and treated as described above and percent survival of the animals was measured. The results are graphed in FIG. 7 and show that huCBE11 #4 is able to induce prolonged survival in vivo in mice with reground tumors.

Example 8

Antibody Affinity Measurement

HT-29 cells were grown in DMEM supplemented with L-guanine, non-essential amino acids, sodium private and 10% fetal bovine serum. Cells were washed once with PBS and removed from the plate by incubating at room temperature for five minutes with PBS plus 20 mM EDTA. Cells were centrifuged at 1000 rpm (110×g) for five minutes and resuspended to a density of 1×10⁷ cells/mL in PBS.

HuCBE11 #4 anti-LTβR antibody and humanized anti-CD40L as a negative control were diluted in PBS and a 12 point serial 1:4 dilution was made to a final concentration range of 2.37 pM–10 µM. 100 µL cell suspension and 100 µL antibody dilution were added together to each well of a 96 well V-bottom micro titer plate. The antibody and the cells were incubated at 4° C. for 2 hours. The plate was centrifuged at 1000 rpm (110×g) for 10 minutes at 4° C. The supernatant was discarded and the cell pellet was washed with cold PBS six times.

Goat-anti human IgG-phycoerythrin conjugate (Jackson Immunoresearch) was diluted 1:100 in PBS and 200 µL was added to each well. The cells were incubated with this secondary antibody for one hour at 4° C., centrifuged as described above, and washed once in cold PBS. The cells were then transferred to polystyrene test tubes. Fluorescence intensity was measured on a FACS Caliber instrument (Beckton Dickinson).

The mean fluorescence intensity values of the staining for anti-CD40L non-specific binding control were plotted against the antibody concentration in Delta Graph. The values were fit to a straight line and the theoretical non-specific binding values for each antibody concentration were subtracted from each data point for the huCBE11 #4 dilution series.

These specific fluorescence intensity values were then plotted against huCBE11 #4 concentrations on a log scale. The resulting curve is bell shaped and symmetrical, and reflects self-inhibition of the antibody binding at high concentrations. The left half of this curve was fit to a four parameter equation to find the functional affinity of the antibody. The resulting curve fit gives an $EC_{50}$ value of 60 pM for the huCBE11 #4 binding to HT-29 cells.

It will be apparent to those skilled in the art that various modifications and variations can be made in the polypeptides, compositions and methods of the invention without departing from the spirit or scope of the invention. Thus, it is intended that the present invention cover the modifications and variations of this invention provided that they come within the scope of the appended claims and their equivalents.

---

What is claimed is:

1. A humanized anti-lymphotoxin-beta receptor (LT-β-R) antibody, or an antigen-binding fragment thereof, comprising
   a light chain variable domain sequence as set forth in SEQ ID NO: 8, and
   a heavy chain comprising complementary determining regions as set forth in SEQ ID NO: 2,
   wherein the antibody comprises at least one of the following residues in its heavy chain: F37, T40, A49, M89 and V93 (Kabat numbering convention), or a conservative amino acid substitution thereof.

2. A humanized anti-lymphotoxin-beta receptor (LT-β-R) antibody, or an antigen-binding fragment thereof, comprising
   a heavy chain variable domain sequence as set forth in SEQ ID NO: 16, and
   a light chain comprising complementary determining regions as set forth in SEQ ID NO: 1, and residue Y71 (Kabat numbering convention), or a conservative amino acid substitution thereof.

3. The humanized antibody of claim 1, wherein the antibody further comprises a heavy chain variable domain sequence as set forth in SEQ ID NO: 16.

4. An antibody, or an antigen-binding fragment thereof, comprising the same heavy and light variable region sequences as an antibody produced by cell line E46.4 (ATCC patent deposit designation PTA-3357) or cell line E77.4 (ATCC patent deposit designation PTA-3765).

5. A humanized anti-lymphotoxin-beta receptor (LT-β-R) antibody comprising a) the light chain amino acid sequence set forth in SEQ ID NO: 32 and
   b) the heavy chain amino acid sequence set forth in SEQ ID NO: 33.

6. A humanized anti-lymphotoxin-beta receptor (LT-β-R) antibody, or an antigen binding fragment thereof, comprising
   a) a light chain variable region comprising complementary determining regions (CDRs) as set forth in SEQ ID NO: 1, and a framework region from a human acceptor light chain, wherein the human acceptor light chain is antibody TNF-A1'CL (Kabat ID 004770), and
   b) a heavy chain variable region comprising CDRs as set forth in SEQ ID NO: 2, and a framework region from a human acceptor heavy chain, wherein the human acceptor heavy chain is antibody FLA-IgG'CL (Kabat ID 040003),
   wherein the framework region of a) or b) comprises at least one framework residue from the mouse CBE11 antibody.

7. The humanized antibody according to any one of claims 1-4 wherein the antibody substantially retains the binding properties of the parent antibody.

8. An immunotoxin comprising the humanized antibody according to any one of claims 1-4, 5 or 6.

9. The humanized antibody according to any one of claims 1-4, 5 or 6, wherein the antibody is linked to a chemotherapeutic drug.

10. A pharmaceutical composition comprising the humanized antibody of any one of claims 1-4, 5 or 6, and a pharmaceutically acceptable carrier.

11. The cell line E46.4 (ATCC patent deposit designation PTA-3357) or cell line E77.4 (ATCC patent deposit designation PTA-3765).

12. A humanized antibody, or antigen binding fragment thereof, comprising
   a) a light chain comprising complementary determining regions (CDRs) as set forth in SEQ ID NO: 1, and residues K3, W41, I46, O69, and Y71 (Kabat numbering convention), or a conservative amino acid substitution thereof, wherein the remainder of the light chain is from a human acceptor framework, and
   b) a heavy chain comprising CDRs as set forth in SEQ ID NO: 2, residues F37, T40, A49, M89, and residue V93 (Kabat numbering convention), or a conservative amino acid substitution thereof, wherein the remainder of the heavy chain is from a human acceptor framework.

13. The humanized antibody of claim 9, wherein the chemotherapeutic drug is selected from the group consisting of adriamycin, 5FU, vinbiastine, actinomycin D, etoposide, cisplatin, methotrexate, and doxorubicin.

14. The humanized antibody of any one of claims 1-4, wherein the antibody is an IgG1.

15. The humanized antibody, or antigen binding fragment thereof, of any one of claims 1-4, wherein the antigen binding fragment is selected from the group consisting of a Fab fragment, an F(ab')$_2$, and an Fv fragment.

16. The humanized anti-lymphotoxin-beta receptor (LT-β-R) antibody, or an antigen binding fragment thereof, of claim 6, wherein the at least one framework residue from the mouse CBE11 antibody is selected from the group consisting of
   i) an unusual murine residue at the interface between the variable light and heavy chains;
   ii) an unusual murine residue close to the antigen binding site; and
   iii) both an unusual murine residue at the interface between the variable light and heavy chains and an unusual murine residue close to the antigen binding site.

17. The humanized antibody, or an antigen binding fragment thereof, of claim 16, wherein the unusual murine residue between the variable light and heavy chains is selected from the group consisting of S34, I46, L89, and H91 in the light chain or Y35, F37, V93, and E95 in the heavy chain.

18. The humanized antibody, or an antigen binding fragment thereof, of claim 16, wherein the unusual murine residue close to the antigen binding site is selected from the group consisting of K3, M11, Y12, W41, Q69, S72, D81, and T83 in the light chain, or F37, T40, E42, A49, and N77 in the heavy chain.

19. The humanized antibody, or an antigen binding fragment thereof, of claim 16, wherein the unusual murine residue at the interface between the variable light and heavy chains and the unusual residue close to the antigen binding site is F37 in the heavy chain.

20. The humanized anti-lymphotoxin-beta receptor (LT-β-R) antibody, or an antigen binding fragment thereof, of any one of claims 4, 5, or 6, wherein the humanized antibody, or antigen-binding fragment thereof, significantly increases survival of an animal in an in vivo tumor growth assay.

21. A humanized anti-lymphotoxin-beta receptor (LT-β-R) antibody, or an antigen binding fragment thereof, comprising a light chain comprising the light chain variable region as set forth in SEQ ID NO: 8, and a heavy chain comprising CDRs as set forth in SEQ ID NO: 2.

22. The humanized antibody of claim 21, wherein the heavy chain further comprises residues F37 and A49 (Kabat numbering convention), or a conservative amino acid substitution thereof, within the framework region.

23. The humanized antibody of claim 21, wherein the heavy chain comprises the heavy chain variable region as set forth in SEQ ID NO: 16.

24. A humanized anti-lymphotoxin-beta receptor (LT-β-R) antibody, or an antigen binding fragment thereof, comprising a light chain comprising CDRs as set forth in SEQ ID NO: 1, and a heavy chain comprising a heavy chain variable region as set forth in SEQ ID NO: 16.

25. A pharmaceutical composition comprising the humanized antibody, or antigen binding fragment thereof, of claim 21 or 24, and a pharmaceutically acceptable carrier.

26. The humanized antibody of claim 21 or 24, wherein the antibody is an IgG1.

27. The humanized antibody, or antigen binding fragment thereof, of claim 21 or 24, wherein the antigen binding fragment is selected from the group consisting of a Fab fragment, an F(ab')$_2$, and an Fv fragment.

28. The humanized antibody of claim 5 or 6, wherein the antibody is an IgG1.

29. The humanized antibody, or antigen binding fragment thereof, of claim 5 or 6, wherein the antigen binding fragment is selected from the group consisting of a Fab fragment, an F(ab')$_2$, and an Fv fragment.

30. The humanized antibody, or antigen-binding fragment of claim 2, further comprising at least one of the following residues in the light chain: K3, W41, I46, and Q69 (Kabat numbering convention), or a conservative amino acid substitution thereof.

31. The humanized antibody, or antigen-binding fragment of claim 2, wherein the antibody further comprises a light chain variable domain sequence as set forth in SEQ ID NO: 8.

32. The humanized antibody of claim 24, wherein the light chain further comprises residue Y71 (Kabat numbering convention), or a conservative amino acid substitution thereof, within the framework region.

33. The humanized antibody of claim 24, wherein the light chain comprises the light chain variable region as set forth in SEQ ID NO: 8.

\* \* \* \* \*

UNITED STATES PATENT AND TRADEMARK OFFICE
CERTIFICATE OF CORRECTION

| | | |
|---|---|---|
| PATENT NO. | : 7,429,644 B2 | Page 1 of 1 |
| APPLICATION NO. | : 10/412406 | |
| DATED | : September 30, 2008 | |
| INVENTOR(S) | : Garber et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,070 days.

Signed and Sealed this
Twenty-third Day of October, 2012

David J. Kappos
*Director of the United States Patent and Trademark Office*